United States Patent
Golobish et al.

(10) Patent No.: US 12,208,116 B2
(45) Date of Patent: *Jan. 28, 2025

(54) MULTI-FUNCTIONAL HEMOCOMPATIBLE POROUS BEAD SORBENT FOR REMOVING PROTEIN BASED TOXINS AND POTASSIUM FROM BIOLOGICAL FLUIDS

(71) Applicant: CytoSorbents, Inc., Princeton, NJ (US)

(72) Inventors: Thomas Golobish, Princeton, NJ (US); Maryann Gruda, Yardley, PA (US); Tamaz Guliashvili, Philadelphia, PA (US); Pamela O'Sullivan, Manalapan, NJ (US); Andrew Scheirer, Hoboken, NJ (US); Vi Dan, East Brunswick, NJ (US); Wei-Tai Young, Hillsborough, NJ (US); Vincent Capponi, Lawrenceville, NJ (US); Phillip Chan, Cherry Hill, NJ (US)

(73) Assignee: CytoSorbents, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/345,683

(22) Filed: Jun. 30, 2023

(65) Prior Publication Data

US 2024/0016830 A1   Jan. 18, 2024

Related U.S. Application Data

(63) Continuation of application No. 17/341,912, filed on Jun. 8, 2021, now Pat. No. 11,723,916, which is a
(Continued)

(51) Int. Cl.
*A61K 31/795*   (2006.01)
*A61K 47/20*   (2006.01)
(Continued)

(52) U.S. Cl.
CPC ............ *A61K 31/795* (2013.01); *A61K 47/20* (2013.01); *A61K 47/26* (2013.01); *A61M 5/165* (2013.01);
(Continued)

(58) Field of Classification Search
None
See application file for complete search history.

(56) References Cited

U.S. PATENT DOCUMENTS

| | | | |
|---|---|---|---|
| 4,297,220 | A | 10/1981 | Meitzner et al. |
| 4,837,015 | A | 6/1989 | Olsen |

(Continued)

FOREIGN PATENT DOCUMENTS

| | | |
|---|---|---|
| CN | 102838780 A | 12/2012 |
| CN | 103497278 A | 1/2014 |

(Continued)

OTHER PUBLICATIONS

Int'l Preliminary Report on Patentability, Oct. 14, 2017, issued in parent matter PCT/US16/58019, filing date of Oct. 21, 2016.
(Continued)

*Primary Examiner* — Dominic Lazaro
(74) *Attorney, Agent, or Firm* — BakerHostetler

(57) ABSTRACT

The invention concerns biocompatible polymer systems comprising at least one polymer with a plurality of pores, said polymer comprising a sulfonic acid salt functionality designed to adsorb a broad range of protein based toxins from less than 0.5 kDa to 1,000 kDa and positively charged ions including but not limited to potassium.

21 Claims, 11 Drawing Sheets

Related U.S. Application Data continuation of application No. 15/769,361, filed as application No. PCT/US2016/058019 on Oct. 21, 2016, now Pat. No. 11,040,061.

(60) Provisional application No. 62/245,071, filed on Oct. 22, 2015.

(51) Int. Cl.

| | | |
|---|---|---|
| *A61K 47/26* | (2006.01) | |
| *A61M 5/165* | (2006.01) | |
| *B01J 20/26* | (2006.01) | |
| *B01J 20/28* | (2006.01) | |
| *B01J 39/20* | (2006.01) | |
| *A61M 1/36* | (2006.01) | |
| *A61M 5/14* | (2006.01) | |

(52) U.S. Cl.
CPC .......... *B01J 20/264* (2013.01); *B01J 20/267* (2013.01); *B01J 20/28069* (2013.01); *B01J 39/20* (2013.01); *A61M 1/3679* (2013.01); *A61M 5/14* (2013.01)

(56) References Cited

U.S. PATENT DOCUMENTS

| | | | |
|---|---|---|---|
| 5,628,730 A | 5/1997 | Shapland et al. | |
| 6,833,153 B1 | 12/2004 | Roorda et al. | |
| 11,040,061 B2* | 6/2021 | Golobish | B01J 20/267 |
| 11,723,916 B2* | 8/2023 | Golobish | B01J 20/28069 |
| | | | 424/78.1 |
| 2002/0042487 A1* | 4/2002 | Deissler | B01J 20/28085 |
| | | | 526/346 |
| 2003/0150813 A1 | 8/2003 | Hayashi et al. | |
| 2007/0021569 A1 | 1/2007 | Willis et al. | |
| 2008/0176966 A1 | 7/2008 | Takagi et al. | |
| 2014/0046023 A1* | 2/2014 | Gottschall | B01J 20/327 |
| | | | 502/7 |

FOREIGN PATENT DOCUMENTS

| | | |
|---|---|---|
| CN | 103533830 A | 1/2014 |
| EP | 0556879 A2 | 8/1993 |
| EP | 0800862 B1 | 2/2002 |
| JP | H08-052209 A | 2/1996 |
| JP | H08-173802 A | 7/1996 |
| JP | H08-299436 A | 11/1996 |
| WO | WO 2012/057185 A1 | 5/2012 |
| WO | WO 2012/094571 A1 | 7/2012 |
| WO | WO 2012/118735 A2 | 9/2012 |
| WO | WO 2014/005039 A2 | 1/2014 |

OTHER PUBLICATIONS

Tsyurupa et al.; Hypercrosslinked Polystyrene: The First Nanoporous Polymeric Material, Nanotechnologies in Russia, 4 (2009), pp. 665-675.

Terai et al.; "Development of a Potassium-Specific Adsorbent for Direct Hemoperfusion"; Artificial Organs; vol. 20; Nov. 1996; p. 1227-1241 (abstract only).

R.L. Albright; "Porous polymers as an anchor for catalysis"; Reactive Polymers, Ion Exchangers, Sorbents; vol. 4; Apr. 1986; p. 155-174 (abstract only).

Akkaramongkolporn et al.; "Preparation and Evaluation of Differently Sulfonated Styrene-Divinylbenzene Cross-linked Copolymer Cationic Exchange Resins as Novel Carriers for Drug Delivery"; AAPS PharmSciTech; vol. 10; Jun. 2009; p. 641-648.

Kolarz et al.; "Hyper-crosslinked sorbents for hemoperfusion"; Die Angewandte Makro. Chemie; vol. 227; 1995; p. 57-68.

Nie et al.; "Novel heparin-mimicking polymer brush grafted carbon nanotube/PES composite membranes for safe and efficient blood purification"; Journal of Membrane Science; vol. 475; 2015; p. 455-468.

\* cited by examiner

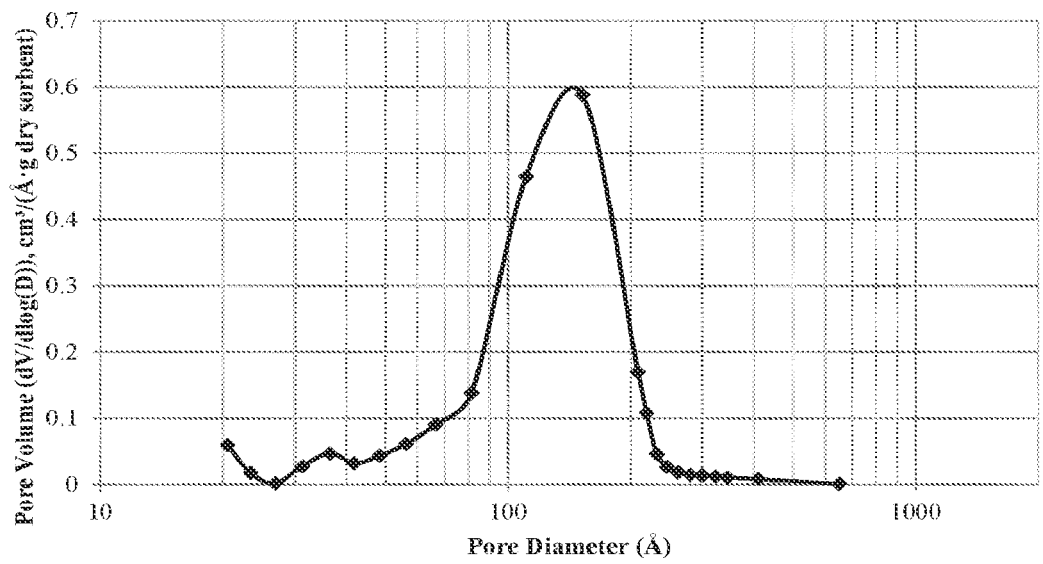

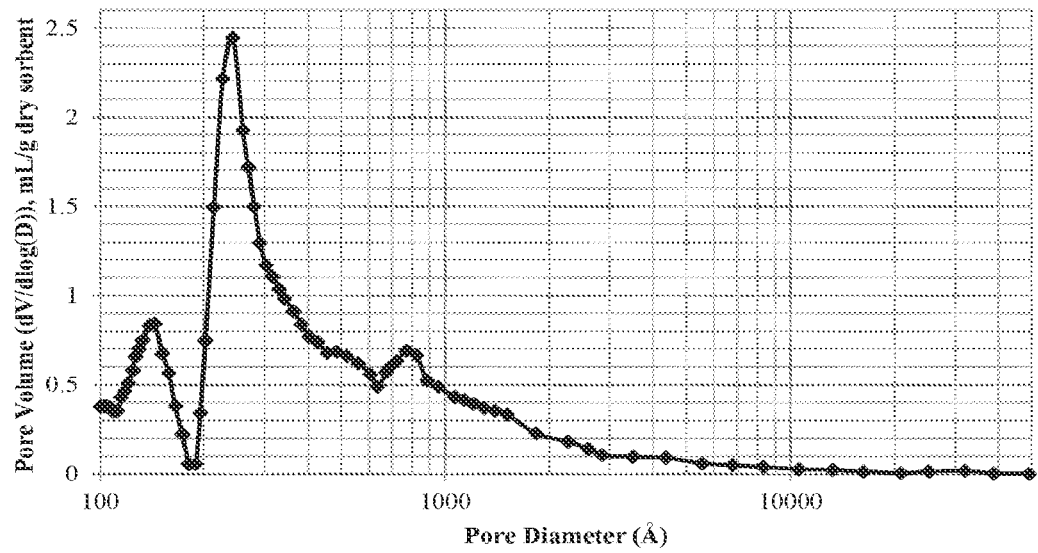

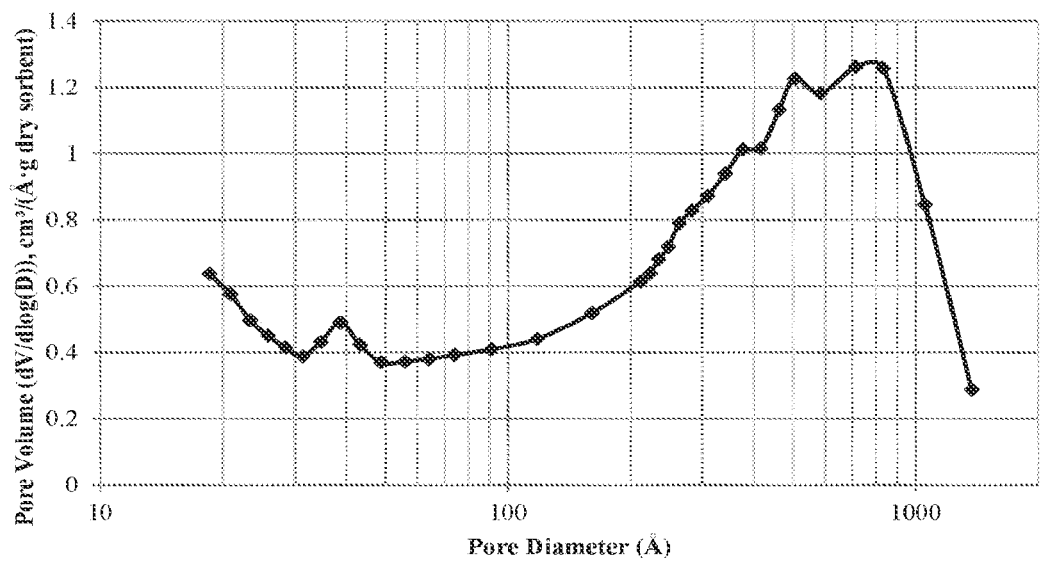

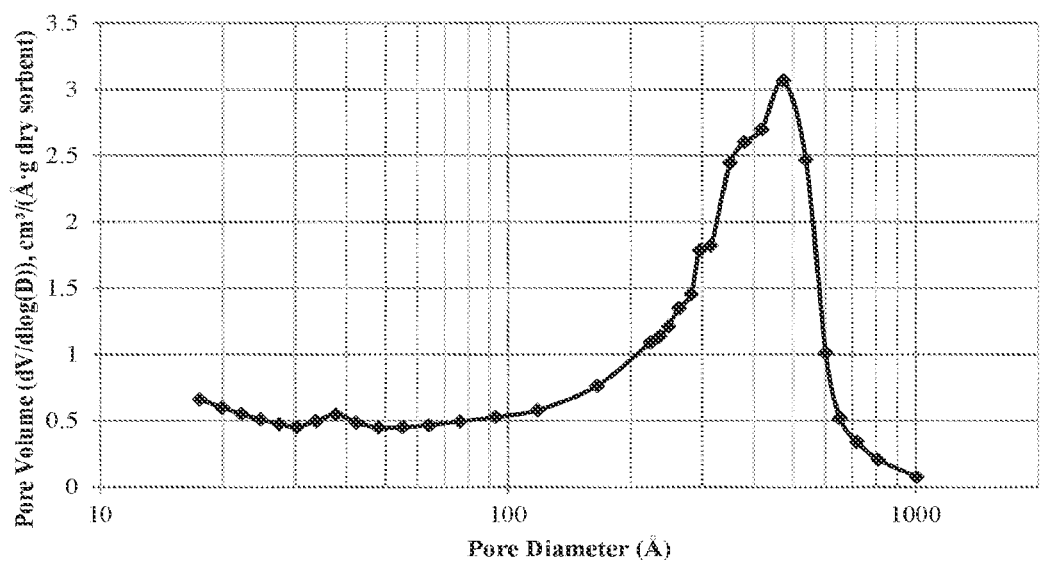

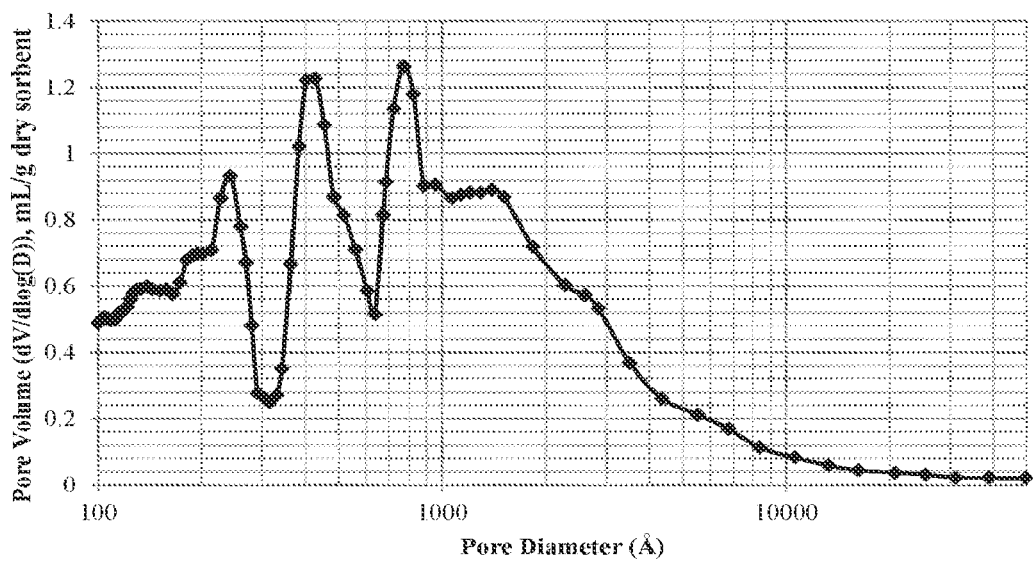

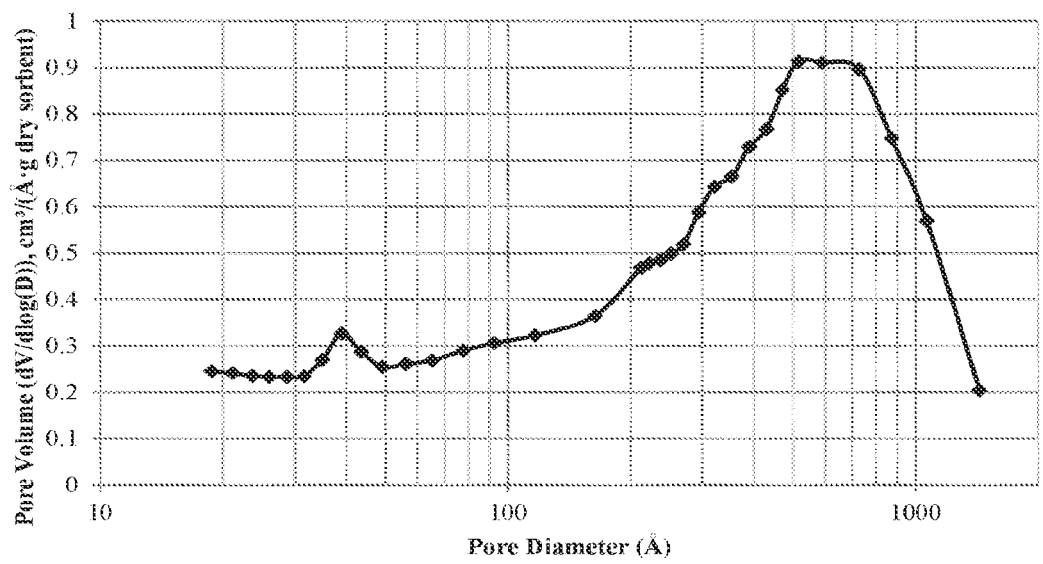

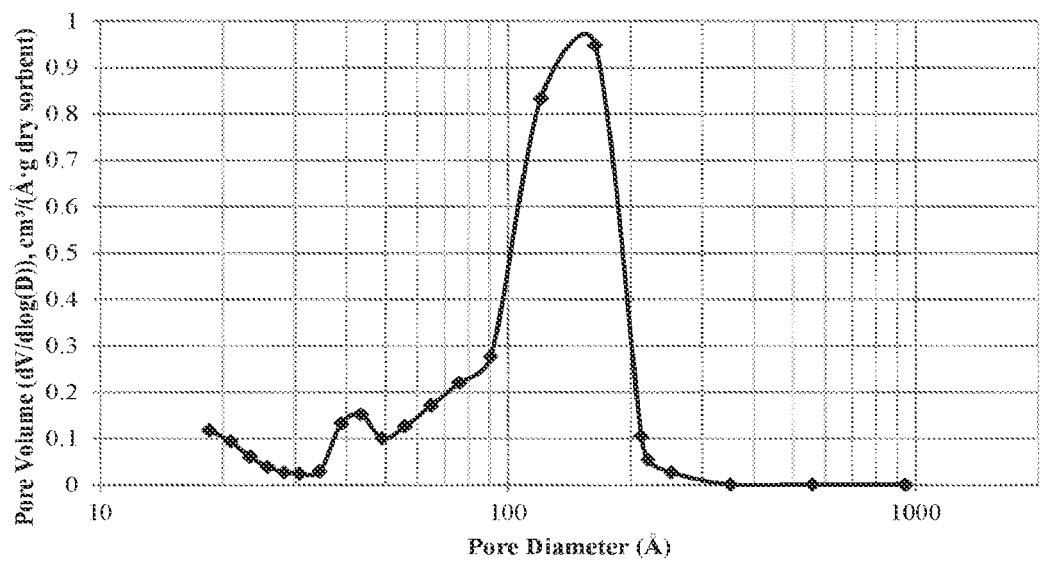

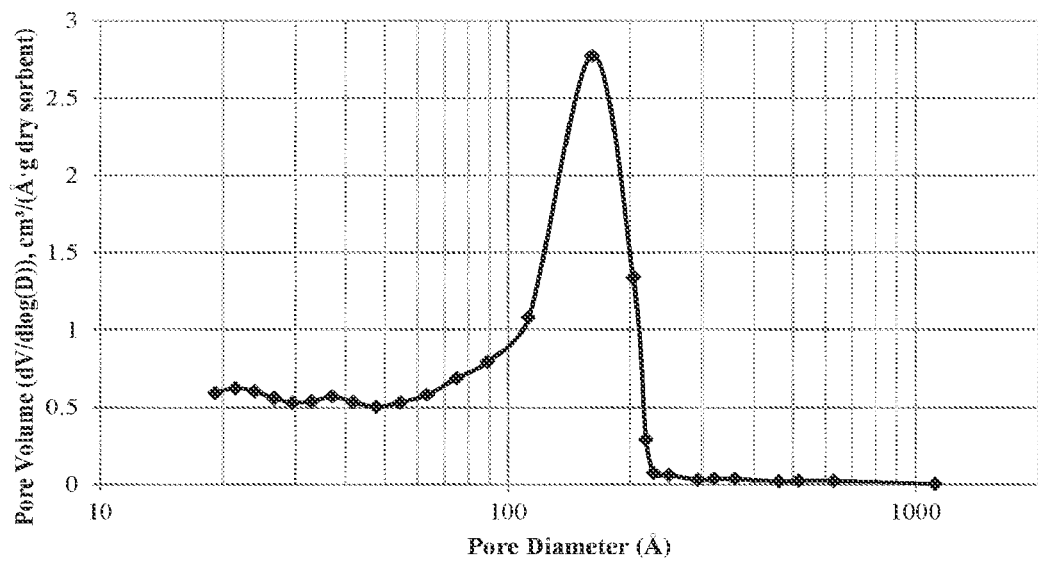

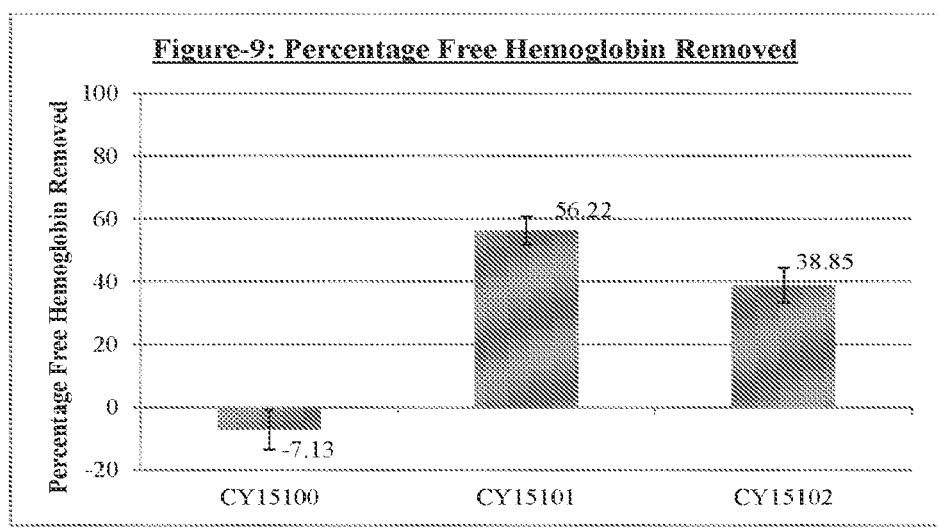

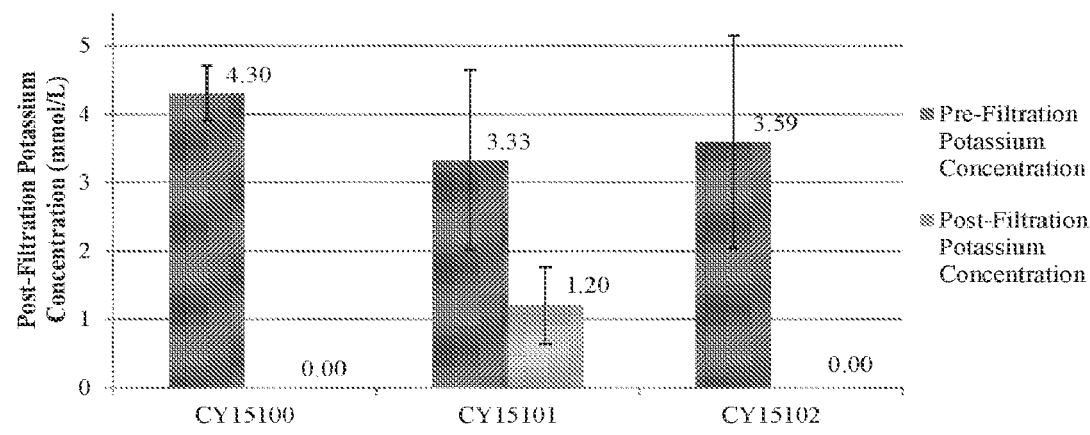

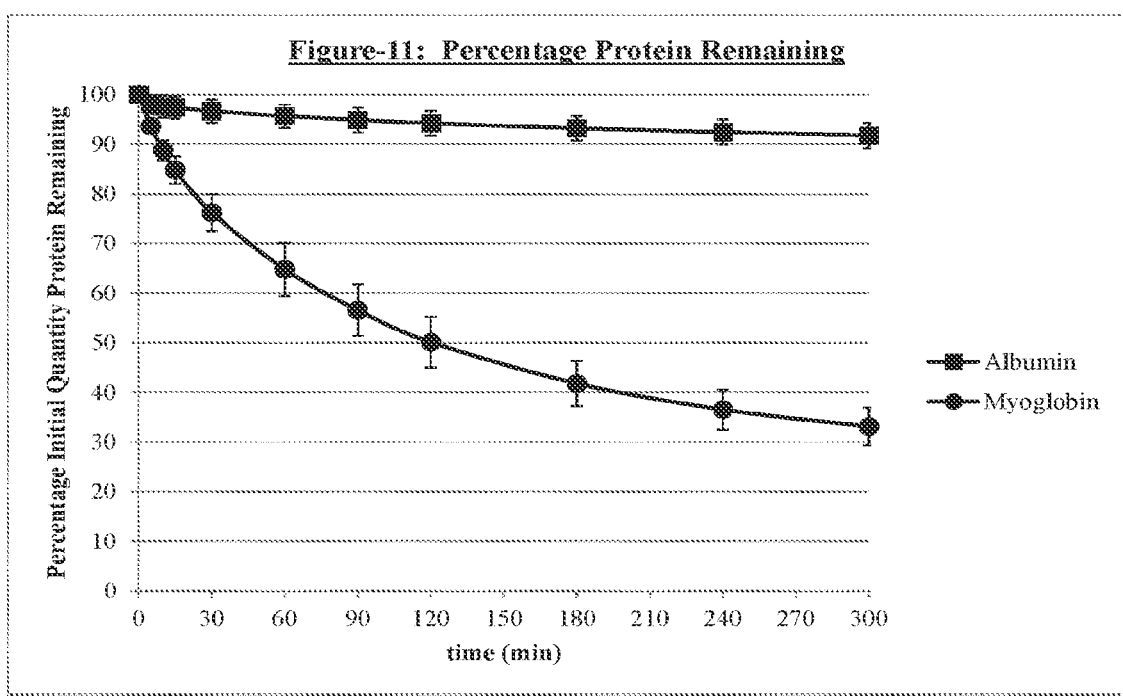

MULTI-FUNCTIONAL HEMOCOMPATIBLE POROUS BEAD SORBENT FOR REMOVING PROTEIN BASED TOXINS AND POTASSIUM FROM BIOLOGICAL FLUIDS

CROSS-REFERENCE TO RELATED APPLICATIONS

The present application is a continuation application of U.S. patent application Ser. No. 17/341,912 filed Jun. 8, 2021, now U.S. Pat. No. 11,723,916, which is a continuation application of U.S. patent application Ser. No. 15/769,361 filed Apr. 19, 2018, now U.S. Pat. No. 11,040,061, which claims priority to International Patent Application No. PCT/US2016/058019 filed Oct. 21, 2016 which claims the benefit of U.S. Provisional Patent Application No. 62/245,071 filed on Oct. 22, 2015. The contents of which are hereby incorporated by reference in their entireties.

GOVERNMENT RIGHTS

The subject matter disclosed herein was made with government support under contract number HHSN268201600006C, awarded by The National Heart, Lung, and Blood Institute (NHLBI). The subject matter disclosed herein was also made with government support under contract number W81XWH-12-C-0038, awarded by The Department of Defense Small Business Innovation Research (DOD-SBIR). The government has certain rights in the herein disclosed subject matter.

TECHNICAL FIELD

The disclosed inventions are in the field of porous polymeric sorbents. The disclosed inventions are also in the field of broadly reducing contaminants in blood and blood products that can cause transfusion reactions; including, but not limited to, potassium, free hemoglobin, cytokines, bioactive lipids, and immunoglobulins. Additionally, the disclosed inventions are in the field of broadly removing contaminants by perfusion or hemoperfusion after tissue destruction; including, but not limited to, potassium, free hemoglobin, free myoglobin, cytokines, bioactive lipids, and immunoglobulins.

BACKGROUND

Packed red blood cell (pRBC) units contain reactive donor antibodies, free hemoglobin, high extracellular potassium levels, and biologically active inflammatory mediators that have the potential to cause adverse effects during blood transfusions. Such adverse effects can include non-hemolytic febrile and allergic transfusion reactions, atypical infections, allo-immunization, and potentially fatal reactions, like transfusion related acute lung injury (TRALI). Furthermore, transfusion risk increases in patients receiving multiple pRBCs, such as those involved in trauma or undergoing surgery, and in primed susceptible patients, such as those in critical care or undergoing high-risk surgery.

The likelihood of adverse effects increases over time for stored blood or blood products, as concentrations of many biological response modifiers, such as potassium, free hemoglobin, and cytokines, increase with storage duration. Cytokines are produced by residual leukocytes during storage of platelets and pRBCs, and can cause inflammation, fever, and direct vascular and organ injury. Erythrocytes contain phosphatidyl choline, and cytosolic and membrane phospholipase A2, contributing increasing levels of lysophosphatidylcholine (lysoPC) during storage. Structural and biochemical changes that RBCs undergo are described as "storage lesion" and lead to a progressive loss of hemoglobin, and potassium. Plasma free hemoglobin can rapidly overwhelm the scavenging capability of haptoglobin, resulting in oxidative damage to lipids, proteins, endothelial cells, tissues, and renal proximal tubules, and in depletion of nitric oxide (NO) upon transfusion. Increases in extracellular potassium during storage lead to an increased risk of hyperkalemia and arrhythmia, particularly for large volume or "massive" transfusions and transfusions in newborns and infants.

Hyperkalemia describes a condition in which the potassium level in the blood exceeds a concentration of 5 mEq/L, where concentrations exceeding 7 mEq/L are considered severe cases. The electrical rhythm of the heart can be altered by moderate hyperkalemia, while severe conditions may cause the heart to stop beating. In addition to blood transfusions, another major cause of hyperkalemia is tissue destruction that causes dying cells to release potassium into blood circulation. Tissue destruction typically results from trauma, burns, hemolysis, massive lysis of tumor cells, rhabdomyolysis, or major surgery, such as cardiac surgery or cardiopulmonary bypass (CPB), where severe tissue destruction leads to more severe cases of hyperkalemia. In addition to the release of potassium into blood circulation, massive tissue injury is characterized by release of a large amount of myoglobin from damaged muscle tissue, plasma free hemoglobin from hemolyzed red blood cells, damage associated molecular pattern (DAMP) factors from damaged cells, and an upregulation of pro- and anti-inflammatory mediators, such as cytokines. Excessive free myoglobin, free hemoglobin, and other inflammatory mediators, can lead to complications such as renal failure or even death. Abnormal regulation of cytokines, or release of DAMPS, may lead to systemic inflammatory response syndrome (SIRS) and multi-organ dysfunction (MODs).

Currently, there are existing technologies for potassium removal, or antibody removal, from stored blood or blood products. Kawasumi Laboratories has developed a single-pass in-line potassium adsorption filter to reduce the risk of hyperkalemia and improve safety for blood transfusions. The filter functions by exchanging potassium ions ($K^+$) for sodium ions ($Na^+$) to decrease the concentration of $K^+$ in stored RBC units. In an in-vitro study conducted by Yamada et. al, 10 filters were tested using each of three AS-3 RBC units via gravity filtration. The mean decrease in potassium was 97.5%, 91.2%, and 64.4% for the first, second, and third units, respectively. Accompanying the decrease in potassium were mean increases of sodium by 33%, magnesium by 151.4%, and total calcium by 116.1%. Plasma hemoglobin was unchanged after filtration.

A journal article published by Terai et. al., titled "Development of a Potassium-Specific Adsorbent for Direct Hemoperfusion", describes a study assessing the development of a sodium/calcium/magnesium exchange resin mixture that removes potassium without associated electrolyte abnormalities. At the time the article was written, direct hemoperfusion over an exchange resin was capable of lowering elevated serum potassium levels, but had not been used clinically due to subsequent electrolyte abnormalities. Prior to evaluating the exchange resin in an in vivo model, batch experiments were conducted in vitro to identify an effective ratio of sodium to calcium to magnesium for the resin mixture. Results from the study demonstrated a reduction of elevated plasma potassium levels from about 6.7 to about 3.5 mEq/L in anephric dogs, without any significant change in levels of sodium, calcium, magnesium, albumin, total protein, or cholesterol, after 2 hours of direct hemoperfusion through an exchange resin column. Pre- and post-hemoperfusion platelet counts and plasma free hemoglobin levels were also measured, where post-hemoperfusion platelet counts were only about 45% of pre-hemoperfusion levels, and there was no significant change in plasma free hemoglobin levels.

Patent WO 2012118735 A2, entitled "Removal of immunoglobulins and leukocytes from biological fluids," discloses devices, systems, and methods, for depleting biological fluids of immunoglobulins and leukocytes. It describes a system comprising immunoglobulin binding media and a leukocyte depletion filter element, where the binding media consist of cellulose beads and are placed into the pre-filtration blood bag. In one example, 30 g dry weight cellulose beads, (4-MEP) HyperCel™ chromatography sorbent (Pall Corporation), were placed in a blood bag to which a unit of 5 day old AS-3 RBC was added, and the blood bag mixed on a rotamixer. The RBCs were gravity filtered through a downstream filter, where beads were trapped in an immunoglobulin binding media chamber and filtered cells passed through a fibrous leukocyte depletion filter before being collected and analyzed. Leukocyte content was reduced by 5.17 log, IgA reduced by 81%, IgG by 98%, and IgM by 42%. In another example, the ability of the leukocyte filter to remove cytokines was examined. Two units of 22-30 day old ABO compatible red cell concentrate were pooled together and then split into two lots. The first was placed in a blood bag containing about 25-33 g dry weight cellulose beads, (4-MEP) HyperCel™ chromatography sorbent (Pall Corporation), with 10 mL PBS and mixed for 45 minutes, and the second passed through a BPF4 High Efficiency leukocyte depletion filter (Pall Corporation) via gravity filtration. Afterwards, both lots were analyzed and it was found that in the aliquot placed in contact with the beads, interleukin 1-Beta (IL-1β) was reduced by 45.7%, interleukin-6 (IL-6) by 26.9%, interleukin-8 (IL-8) by 57.1% and tissue necrosis factor-alpha (TNF-α) by 49.9% For the aliquot passed through the filter, IL-1β was not reduced, IL-6 was not reduced, IL-8 was reduced by 35.0% and TNF-α reduced by 7.5%

In a journal article by Silliman et. al., it was demonstrated that pre-storage filtration of packed RBCs removes HLA and HNA antibodies, reducing pro-inflammatory activity in RBC supernatant in an animal TRALI model. In the described study, plasma that contained antibodies to human lymphocyte antigen (HLA)-A2, or human neutrophil antigen (HNA)-3a, was filtered and priming activities of specific HNA-3a and HLA-2a were measured. OX27 antibodies were added to plasma and filtration was analyzed using a 2-event animal model for TRALI. RBC units from 31 donors, who were known to possess antibodies against HLA antigens, were filtered. In addition, 4 RBC units underwent standard leukoreduction. PMN priming activity, immunoglobulins, HLA antibodies, and ability to induce TRALI were measured. Filtration of the plasma was shown to remove more than 96% of IgG, and antibodies to HLA-A2 and HNA-3a, including their respective priming activity, and mitigated in vivo TRALI. Antibodies to HLA antigens were removed in experimental filtration of RBC units, accompanied by an inhibition of accumulation of lipid priming activity and lipid-mediated TRALI.

The sorbent material described herein is uniquely designed to efficiently remove free hemoglobin, antibodies, bioactive lipids, cytokines, and potassium, from blood and blood products. The polymer is multi-functional, retaining said biomolecules through tortuous path, sorption, pore capture, and ion exchange mechanisms. Novel chemistry is used to synthesize the polymer, utilizing a controlled sulfonation procedure that allows for the incorporation of sulfonic acid groups onto the aromatic rings without oxidizing all residual double bonds. This allows the polymeric matrix to maintain protein sorption and ion exchange capabilities, while still leaving residual functional groups available for hemocompatibility improvement modifications. The balance between sulfonation and retention of residual double bonds is crucial for preparation of an effective polymer sorbent.

Differentiating the multi-functional polymer from other filters that remove only reactive proteins or only potassium is its ability to remove both simultaneously without sacrificing binding capacity for either. Additionally, the sorbent is able to remove cytokines and inflammatory protein moieties simultaneously while removing potassium and antibodies. For hemoperfusion applications, it is a requirement that the polymer is hemocompatible. Using the unactivated partial thromboplastin time (uPTT) assay as a measure of thrombogenicity, the polymer described herein exhibits minimal activation, indicating a plasma-like interaction. This polymer is suited for a wide variety of applications, as many cases of trauma, burn, and major surgery, result in hyperkalemia, cytokine storm, and require blood transfusions. The ability to use one multi-application filter has many advantages over using many single-application filters. Given the value of blood and blood products, the use of a single, smaller filter that minimizes cell loss within the retained volume and reduces complexity of material quality assurance is very desirable.

SUMMARY

In some aspects, the invention concerns biocompatible polymer system comprising at least one polymer, said polymer comprising (i) a plurality of pores and (ii) a sulfonic acid salt functionality; the polymer system capable of adsorbing (i) a broad range of protein based toxins having a molecular weight of from less than about 0.5 kDa to about 1,000 kDa (or about 1 kDa to about 1,000 kDa in some embodiments) and (ii) positively charged ions. Some polymer systems have a polymer pore structure that has a total volume of pore sizes in the range of from 10 Å to 40,000 Å greater than 0.1 cc/g and less than 5.0 cc/g dry polymer. Some preferred polymers are hemocompatible. The polymer system has the form of a solid support. Certain preferred polymer systems have a geometry of a spherical bead. Other polymer systems have the form of a fiber, monolithic column, film, membrane, or semi-permeable membrane.

In some embodiments, the toxins adsorbed comprise one or more of inflammatory mediators and stimulators comprised of one or more of cytokines, superantigens, monokines, chemokines, interferons, proteases, enzymes, peptides including bradykinin, soluble CD40 ligand, bioactive lipids, oxidized lipids, cell-free hemoglobin, cell-free myoglobin, growth factors, glycoproteins, prions, toxins, bacterial and viral toxins, endotoxins, drugs, vasoactive substances, foreign antigens, antibodies, and positively charged ions. In some preferred embodiments, the positively charged ion is potassium.

The polymers can be made by any means known in the art to produce a suitable porous polymer. In some embodiments, the polymer is made using suspension polymerization. Some polymers comprise a hypercrosslinked polymer. Certain spherical beads have a biocompatible hydrogel coating. In certain embodiments, the polymer is in the form of hyper-crosslinked or a macroreticular porous polymer beads that have been sulfonated under mild conditions that retain residual functionality of any unreacted double bonds and chloromethyl groups. The unreacted double bonds or chloromethyl groups can be modified via free radical or $S_N2$ type chemistry to attach one or more of biocompatible and hemocompatible monomers, cross-linkers or low molecular weight oligomers.

In some embodiments, the porous polymer beads comprise sulfonic acid groups or a salt thereof, sulfonyl chloride, or sulfonate ester groups. The polymer beads comprising sulfonic acid groups or a salt thereof, sulfonyl chloride, or sulfonate ester groups can be produced by graft copolymerization of (i) premade porous polymer that contains unreacted double bonds with (ii) polymerizable vinyl monomers containing sulfonic acid groups or a salt thereof to form a mixture comprising hemocompatible vinyl monomers.

Some polymer systems are constructed from polymerizable vinyl monomers containing sulfonic acid groups or a salt thereof which are copolymerized in the presence of cross-linker, hemocompatible monomer, monomer and suitable porogen to yield porous polymeric polymer containing a sulfonic acid salt functionality.

Certain polymers are formed and subsequently modified to be biocompatible. Some modifications comprise forming a biocompatible surface coating or layer.

Other aspects include methods of perfusion comprising passing a physiologic fluid once through or by way of a suitable extracorporeal circuit through a device comprising the biocompatible polymer system described herein.

Yet another aspect concerns devices for removing (i) a broad range of protein based toxins from less than 0.5 kDa to 1,000 kDa and (ii) positively charged ions from physiologic fluid comprising the biocompatible polymer system described herein.

BRIEF DESCRIPTION OF THE DRAWINGS

The accompanying drawings, which are included to provide a further understanding of the disclosure, are incorporated in and constitute a part of this specification, illustrate aspects of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings:

FIGS. 1, 2 and 3 present log differential pore volume plots for CY15100 and CY15102.

FIGS. 4, 5 and 6 show plots of log differential pore volume for modified polymers.

FIGS. 7 and 8 show plots of log differential pore volume for polymers CY15048 and CY15049.

FIG. 9 presents the percentage of initial free hemoglobin removed during single-pass filtration, averaged from three trials FIG. 10 displays pre- and post-filtration potassium ion concentration in blood, averaged from three trials.

FIG. 11 presents dynamic recirculation data for CY14144, averaged from 7 trials.

DETAILED DESCRIPTION OF ILLUSTRATIVE EMBODIMENTS

As required, detailed embodiments of the present invention are disclosed herein; it is to be understood that the disclosed embodiments are merely exemplary of the invention that may be embodied in various forms. Therefore, specific structural and functional details disclosed herein are not to be interpreted as limits, but merely as a basis for teaching one skilled in the art to employ the present invention. The specific examples below will enable the invention to be better understood. However, they are given merely by way of guidance and do not imply any limitation.

The present invention may be understood more readily by reference to the following detailed description taken in connection with the accompanying figures and examples, which form a part of this disclosure. It is to be understood that this invention is not limited to the specific materials, devices, methods, applications, conditions or parameters described and/or shown herein, and that the terminology used herein is for the purpose of describing particular embodiments by way of example only and is not intended to be limiting of the claimed invention. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further reference to values stated in ranges includes each and every value within that range.

The following definitions are intended to assist in understanding the present invention:

The term "biocompatible" is defined to mean the sorbent is capable of coming in contact with physiologic fluids, living tissues, or organisms, without producing unacceptable clinical changes during the time that the sorbent is in contact with the physiologic fluids, living tissues, or organisms.

The term "hemocompatible" is defined as a condition whereby a biocompatible material when placed in contact with whole blood or blood plasma results in clinically acceptable physiologic changes.

As used herein, the term "physiologic fluids" are liquids that originate from the body and can include, but are not limited to, nasopharyngeal, oral, esophageal, gastric, pancreatic, hepatic, pleural, pericardial, peritoneal, intestinal, prostatic, seminal, vaginal secretions, as well as tears, saliva, lung, or bronchial secretions, mucus, bile, blood, lymph, plasma, serum, synovial fluid, cerebrospinal fluid, urine, and interstitial, intracellular, and extracellular fluid, such as fluid that exudes from burns or wounds.

As used herein, the term "laboratory or manufacturing fluids" are defined as liquids that are used in life sciences applications that include, but are not limited to, tissue and cell culture media and additives, chemical or biologic assay media, sample preparation buffers, biologic manufacturing media, growth media, and bioreactor media.

As used herein, the term "sorbent" includes adsorbents and absorbents.

For purposes of this invention, the term "sorb" is defined as "taking up and binding by absorption and adsorption".

For the purposes of this invention, the term "perfusion" is defined as passing a physiologic fluid, once through or by way of a suitable extracorporeal circuit, through a device containing the porous polymeric adsorbent to remove toxic molecules from the fluid.

The term "hemoperfusion" is a special case of perfusion where the physiologic fluid is blood.

The term "dispersant" or "dispersing agent" is defined as a substance that imparts a stabilizing effect upon a finely divided array of immiscible liquid droplets suspended in a fluidizing medium.

The term "heparin mimicking polymer" refers to any polymer that possesses the same anticoagulant and/or anti-thrombogenic properties as heparin.

The term "macroreticular synthesis" is defined as a polymerization of monomers into polymer in the presence of an inert precipitant which forces the growing polymer molecules out of the monomer liquid at a certain molecular size dictated by the phase equilibria to give solid nanosized microgel particles of spherical or almost spherical symmetry packed together to give a bead with physical pores of an open cell structure [U.S. Pat. No. 4,297,220, Meitzner and Oline, Oct. 27, 1981; R. L. Albright, Reactive Polymers, 4, 155-174 (1986)].

The term "hypercrosslinked" describes a polymer in which the single repeating unit has a connectivity of more than two. Hypercrosslinked polymers are prepared by cross-linking swollen, or dissolved, polymer chains with a large number of rigid bridging spacers, rather than copolymerization of monomers. Crosslinking agents may include bis (chloromethyl) derivatives of aromatic hydrocarbons, methylal, monochlorodimethyl ether, and other bifunctional compounds that react with the polymer in the presence of Friedel-Crafts catalysts [Tsyurupa, M. P., Z. K. Blinnikova, N. A. Proskurina, A. V. Pastukhov, L. A. Pavlova, and V. A. Davankov. "Hypercrosslinked Polystyrene: The First Nanoporous Polymeric Material." *Nanotechnologies in Russia* 4 (2009): 665-75.]

Some preferred polymers comprise residues from one or more monomers, or containing monomers, or mixtures thereof, selected from acrylonitrile, allyl ether, allyl glycidyl ether, butyl acrylate, butyl methacrylate, cetyl acrylate, cetyl methacrylate, 3,4-dihydroxy-1-butene, dipentaerythritol diacrylate, dipentaerythritol dimethacrylate, dipentaerythritol tetraacrylate, dipentaerythritol tetramethacrylate, dipentaerythritol triacrylate, dipentaerythritol trimethacrylate, divinylbenzene, divinylformamide, divinylnaphthalene, divinylsulfone, 3,4-epoxy-1-butene, 1,2-epoxy-9-decene, 1,2-epoxy-5-hexene, ethyl acrylate, ethyl methacrylate, ethylstyrene, ethylvinylbezene, glycidyl methacrylate, methyl acrylate, methyl methacrylate, octyl acrylate, octyl methacrylate, pentaerythritol diacrylate, pentaerythritol dimethacrylate, pentaerythritol tetraacrylate, pentaerythritol tetramethacrylate, pentaerythritol triacrylate, pentaerythritol trimethacrylate, styrene, trimethylolpropane diacrylate, trimethylolpropane dimethacrylate, trimethylolpropane triacrylate, trimethylolpropane trimethacrylate, trivinylbenzene, trivinylcyclohexane, vinyl acetate, vinylbenzyl alcohol, 4-vinyl-1-cyclohexene 1,2-epoxide, vinylformamide, vinylnaphthalene, 2-vinyloxirane, and vinyltoluene.

Some embodiments of the invention use an organic solvent and/or polymeric porogen as the porogen or pore-former, and the resulting phase separation induced during polymerization yield porous polymers. Some preferred porogens are selected from, or mixtures comprised of any combination of, benzyl alcohol, cyclohexane, cyclohexanol, cyclohexanone, decane, dibutyl phthalate, di-2-ethylhexyl phthalate, di-2-ethylhexylphosphoric acid, ethylacetate, 2-ethyl-1-hexanoic acid, 2-ethyl-1-hexanol, n-heptane, n-hexane, isoamyl acetate, isoamyl alcohol, n-octane, pentanol, poly(propylene glycol), polystyrene, poly(styrene-co-methyl methacrylate), tetraline, toluene, tri-n-butylphosphate, 1,2,3-trichloropropane, 2,2,4-trimethylpentane, xylene.

In yet another embodiment, the dispersing agent is selected from a group consisting of hydroxyethyl cellulose, hydroxypropyl cellulose, poly(diethylaminoethyl acrylate), poly(diethylaminoethyl methacrylate), poly(dimethylaminoethyl acrylate), poly(dimethylaminoethyl methacrylate), poly(hydroxyethyl acrylate), poly(hydroxyethyl methacrylate), poly(hydroxypropyl acrylate), poly(hydroxypropyl methacrylate), poly(vinyl alcohol), salts of poly(acrylic acid), salts of poly(methacrylic acid) and mixtures thereof.

Preferred sorbents are biocompatible. In another further embodiment, the polymer is biocompatible. In yet another embodiment, the polymer is hemocompatible. In still a further embodiment, the biocompatible polymer is hemocompatible. In still a further embodiment, the geometry of the polymer is a spherical bead.

In another embodiment, the biocompatible polymer comprises poly(N-vinylpyrrolidone).

The coating/dispersant on the porous poly(styrene-co-divinylbenzene) resin will imbue the material with improved biocompatibility.

In still yet another embodiment, a group of cross-linkers consisting of dipentaerythritol diacrylates, dipentaerythritol dimethacrylates, dipentaerythritol tetraacrylates, dipentaerythritol tetramethacrylates, dipentaerythritol triacrylates, dipentaerythritol trimethacrylates, divinylbenzene, divinylformamide, divinylnaphthalene, divinylsulfone, pentaerythritol diacrylates, pentaerythritol dimethacrylates, pentaerythritol tetraacrylates, pentaerythritol tetramethacrylates, pentaerythritol triacrylates, pentaerythritol trimethacrylates, trimethylolpropane diacrylate, trimethylolpropane dimethacrylate, trimethylolpropane triacrylate, trimethylolpropane trimethacrylate, trivinylbenzene, trivinylcyclohexane and mixtures thereof can be used in formation of a hemocompatible hydrogel coating.

In some embodiments, the polymer is a polymer comprising at least one crosslinking agent and at least one dispersing agent. The dispersing agent may be biocompatible. The dispersing agents can be selected from chemicals, compounds or materials such as hydroxyethyl cellulose, hydroxypropyl cellulose, poly(diethylaminoethyl acrylate), poly(diethylaminoethyl methacrylate), poly(dimethylaminoethyl acrylate), poly(dimethylaminoethyl methacrylate), poly(hydroxyethyl acrylate), poly(hydroxyethyl methacrylate), poly(hydroxypropyl acrylate), poly(hydroxypropyl methacrylate), poly(vinyl alcohol), salts of poly(acrylic acid), salts of poly(methacrylic acid) and mixtures thereof; the crosslinking agent selected from a group consisting of dipentaerythritol diacrylates, dipentaerythritol dimethacrylates, dipentaerythritol tetraacrylates, dipentaerythritol tetramethacrylates, dipentaerythritol triacrylates, dipentaerythritol trimethacrylates, divinylbenzene, divinylformamide, divinylnaphthalene, divinylsulfone, pentaerythritol diacrylates, pentaerythritol dimethacrylates, pentaerythritol tetraacrylates, pentaerythritol tetramethacrylates, pentaerythritol triacrylates, pentaerythritol trimethacrylates, trimethylolpropane diacrylate, trimethylolpropane dimethacrylate, trimethylolpropane triacrylate, trimethylolpropane trimethacrylate, trivinylbenzene, trivinylcyclohexane and mixtures thereof. Preferably, the polymer is developed simultaneously with the formation of the coating, wherein the dispersing agent is chemically bound or entangled on the surface of the polymer.

In still another embodiment, the biocompatible polymer coating is selected from a group consisting of poly(hydroxyethyl methacrylate), poly(hydroxyethyl acrylate), poly(dimethylaminoethyl methacrylate), salts of poly(acrylic acid), salts of poly(methacrylic acid), poly(diethylaminoethyl methacrylate), poly(hydroxypropyl methacrylate), poly(hydroxypropyl acrylate), poly(N-vinylpyrrolidone), poly(vinyl alcohol) and mixtures thereof. In another embodiment, the salts may be sodium and potassium salts and in still another embodiment, the salts are water-soluble salts.

In still another embodiment, the biocompatible oligomer coating is selected from a group consisting of poly(hydroxyethyl methacrylate), poly(hydroxyethyl acrylate), poly(dimethylaminoethyl methacrylate), salts of poly(acrylic acid), salts of poly(methacrylic acid), poly(diethylaminoethyl methacrylate), poly(hydroxypropyl methacrylate), poly(hydroxypropyl acrylate), poly(N-vinylpyrrolidone), poly(vinyl alcohol) and mixtures thereof. In another embodiment, the salts may be sodium and potassium salts and in still another embodiment, the salts are water-soluble salts.

The present biocompatible sorbent compositions are comprised of a plurality of pores. The biocompatible sorbents are designed to adsorb a broad range of toxins from less than 0.5 kDa to 1,000 kDa. While not intending to be bound by theory, it is believed the sorbent acts by sequestering molecules of a predetermined molecular weight within the pores. The size of a molecule that can be sorbed by the polymer will increase as the pore size of the polymer increases. Conversely, as the pore size is increased beyond the optimum pore size for adsorption of a given molecule, adsorption of said protein may or will decrease.

In certain methods, the solid form is porous. Some solid forms are characterized as having a pore structure having a total volume of pore sizes in the range of from 10 Å to 40,000 Å greater than 0.1 cc/g and less than 5.0 cc/g dry polymer.

In certain embodiments, the polymers can be made in bead form having a diameter in the range of 0.1 micrometers to 2 centimeters. Certain polymers are in the form of powder, beads or other regular or irregularly shaped particulates.

In some embodiments, the plurality of solid forms comprises particles having a diameter in the range for 0.1 micrometers to 2 centimeters.

In some methods, the undesirable molecules are inflammatory mediators and stimulators comprised of cytokines, superantigens, monokines, chemokines, interferons, proteases, enzymes, peptides including bradykinin, soluble CD40 ligand, bioactive lipids, oxidized lipids, cell-free hemoglobin, damage-associated molecular pattern (DAMPs), Pathogen-associated molecular pattern molecules (PAMPs), cell-free myoglobin, growth factors, glycoproteins, prions, toxins, bacterial and viral toxins, endotoxins, drugs, vasoactive substances, foreign antigens, antibodies, and positively charged ions, including, but not limited to, potassium.

In some methods, the antibodies can be immunoglobulin A (IgA), immunoglobulin D (IgD), immunoglobulin E (IgE), immunoglobulin D (IgG), immunoglobulin D (IgM) and/or immunoglobulin fragments or subunits.

DAMPs have been associated with countless syndromes and diseases. These include complications from trauma, burns, traumatic brain injury and invasive surgery, and also organ-specific illnesses like liver disease, kidney dialysis complications, and autoimmune diseases. DAMPs are host molecules that can initiate and perpetuate noninfectious SIRS and exacerbate infectious SIRS. DAMPs are a diverse family of molecules that are intracellular in physiological conditions and many are nuclear or cytosolic proteins. DAMPs can be divided into two groups: (1) molecules that perform noninflammatory functions in living cells (such as HMGB1) and acquire immunomodulatory properties when released, secreted, modified, or exposed on the cell surface during cellular stress, damage, or injury, or (2) alarmins, i.e., molecules that possess cytokine-like functions (such as β-Defensins and Cathelicidin), which can be stored in cells and released upon cell lysis, whereupon they contribute to the inflammatory response. When released outside the cell or exposed on the surface of the cell following tissue injury, they move from a reducing to an oxidizing milieu, which affects their activity. Also, following necrosis, mitochondrial and nuclear DNA fragments are released outside the cell becoming DAMPs.

DAMPs, such as HMGB-1, heat-shock and S100 proteins are normally found inside cells and are released by tissue damage. DAMPs act as endogenous danger signals to promote and exacerbate the inflammatory response. HMGB-1 is a non-histone nuclear protein that is released under stress conditions. Extracellular HMGB-1 is an indicator of tissue necrosis and has been associated with an increased risk of sepsis and multiple organ dysfunction syndrome (MODS). S100 A8 (granulin A, MRP8) and A9 (granulin B\, MRP14) homo and heterodimers bind to and signal directly via the TLR4/lipopolysaccharide receptor complex where they become danger signals that activate immune cells and vascular endothelium. Procalcitonin is a marker of severe sepsis caused by bacteria and its release into circulation is indicative of the degree of sepsis. Serum amyloid A (SAA), an acute-phase protein, is produced predominantly by hepatocytes in response to injury, infection, and inflammation. During acute inflammation, serum SAA levels may rise by 1000-fold. SAA is chemotactic for neutrophils and induces the production of proinflammatory cytokines. Heat shock proteins (HSP) are a family of proteins that are produced by cells in response to exposure to stressful conditions and are named according to their molecular weight (10, 20-30, 40, 60, 70, 90). The small 8-kilodalton protein ubiquitin, which marks proteins for degradation, also has features of a heat shock protein. Hepatoma-derived growth factor (HDGF), despite its name, is a protein expressed by neurons. HDGF can be released actively by neurons via a nonclassical pathway and passively by necrotic cells. Other factors, such as complement factors 3 and 5, are activated as part of the host defense against pathogens but can also contribute to the adverse outcomes in sepsis. Excessive, persistent circulating levels of cytokines and DAMPs contribute to organ injury and identify those patients who have the highest risk of multiple organ dysfunction (MODs) and death in community acquired pneumonia and sepsis.

PAMPs include lipopolysaccharides, lipopeptides, lipoteichoic acid, peptidoglycans, nucleic acids such as double-stranded RNA, toxins and flagellins and can trigger an immune response in the host (e.g. the innate immune system) to fight the infection, leading to the production of high levels of inflammatory and anti-inflammatory mediators, such as cytokines. PAMPs and high cytokine levels, as well as direct tissue injury (trauma, burns, etc.), can damage tissue, causing the extracellular release of damage-associated molecular pattern (DAMPs) molecules into the bloodstream. DAMPs are a broad class of endogenous molecules, which like PAMPs, trigger the immune response through pattern recognition receptors (PRRs) such as Toll-like receptors (TLRs).

Preferred sorbents include cross-linked polymeric material derived from the reaction of a cross-linker with one or more of the following polymerizable monomers, then subsequently sulfonated to form a sulfonic acid salt: acrylonitrile, butyl acrylate, butyl methacrylate, cetyl acrylate, cetyl methacrylate, divinylbenzene, ethyl acrylate, ethyl methacrylate, ethylstyrene, methyl acrylate, methyl methacrylate, octyl acrylate, octyl methacrylate, styrene, vinylbenzyl alcohol, vinylformamide, vinylnaphthalene, or vinyltoluene.

In some embodiments, radically polymerizable vinyl monomers containing —$SO_3Na$ groups, or ~$SO_3H$ groups, can be used in graft copolymerization with porous polymers containing polymerizable double bonds. These monomers can be selected from 4-styrene sulfonic acid sodium salt, vinyl sulfonic acid sodium salt, 2-acrylamido-2-methyl-1-propanesulfonic acid, 2-acrylamido-2-methyl-1-propanesulfonic sodium salt, 3-sulfopropyl acrylate sodium salt, 3-sulfopropyl methacrylate sodium salt, [2-(methacryloyloxy)ethyl] dimethyl-(3-sulfopropyl)ammonium hydroxide, N-(3-sulfopropyl)-N-(methacryloxyethyl)-N,N-dimethylammonium betaine, para-styrene sulfonyl chloride, or any combinations thereof. Furthermore, para-styrene sulfonyl chloride can be polymerized in the presence of divinylbenzene and hydrolyzed with sodium hydroxide solution to directly yield poly(styrene-co-divinylbenzene) porous material with ~$SO_3Na$ groups.

In another embodiment, the present invention relates to a sulfonated polymer comprised of at least one crosslinking agent for making the polymer and at least one dispersing agent whereby the dispersing agent forms a biocompatible surface on the polymer.

In one embodiment the porous polymers of this invention are made by suspension polymerization in a formulated aqueous phase with free radical initiation in the presence of aqueous phase dispersants that are selected to provide a biocompatible and a hemocompatible exterior surface to the formed polymer beads. The sulfonation of the resultant beads yields an ion exchange resin coated with a hemocompatible hydrogel. The beads are made porous by the macroreticular synthesis with an appropriately selected porogen (pore forming agent) and an appropriate time-temperature profile for the polymerization in order to develop the proper pore structure. The subsequent introduction of the sulfonic acid groups in the already formed network forms a sulfonic acid salt inner core (ion exchange resin) and a hemocompatible outer hydrogel exterior. Suitable choice of the reaction conditions for the sulfonation allows preservation or expression (via a protecting group) of the hemocompatible nature of the exterior hydrogel.

In another embodiment polymers made by suspension polymerization can be made biocompatible and hemocompatible by further grafting of biocompatible and hemocompatible monomers or low molecular weight oligomers. It has been shown that the radical polymerization procedure does not consume all the vinyl groups of DVB introduced into copolymerization. On average, about 30% of DVB species fail to serve as crosslinking bridges and remain involved in the network by only one of two vinyl groups. The presence of a relatively high amount of pendant vinyl groups is therefore a characteristic feature of the macroporous adsorbents. It can be expected that these pendant vinyl groups are preferably exposed to the surface of the polymer beads and their macropores should be readily available to chemical modification. The chemical modification of the surface of macroporous DVB-copolymers relies on chemical reactions of the surface-exposed pendant vinyl groups and aims at converting these groups into more hydrophilic functional groups. This conversion via free radical grafting of monomers and/or cross-linkers or low molecular weight oligomers provides the initial hydrophobic adsorbing material with the property of hemocompatibility. The subsequent introduction of the sulfonic acid groups into the already formed network forms a sulfonic acid salt inner core (ion exchange resin) and a hemocompatible outer hydrogel exterior. Suitable choice of the reaction conditions for the sulfonation allows preservation or expression (via a protecting group) of the hemocompatible nature of the exterior hydrogel.

Still another embodiment consists of binding long hydrophilic polymer chains onto the beads' surfaces, which should preclude contact between blood cells and the sulfonated polystyrene surface. This can be accomplished via free radical or $S_N2$ type chemistry. The chemical modification of the surface of sorbent beads, which is the case in the above modification, is facilitated by the remarkable peculiarity of the hypercrosslinked polystyrene; namely, that the reactive functional groups of the polymer are predominantly located on its surface. The hypercrosslinked polystyrene is generally prepared by crosslinking polystyrene chains with large amounts of bifunctional compounds, in particular, those bearing two reactive chloromethyl groups. The latter alkylate, in a two-step reaction, two phenyl groups of neighboring polystyrene chains according to Friedel-Crafts reaction, with evolution of two molecules of HCl and formation of a cross bridge. During the crosslinking reaction, the three-dimensional network formed acquires rigidity. This property gradually reduces the rate of the second step of the crosslinking reaction, since the reduced mobility of the second pendant functional group of the initial crosslinking reagent makes it more and more difficult to add an appropriate second partner for the alkylation reaction. This is especially characteristic of the second functional groups that happen to be exposed to the surface of the bead. Therefore, of the pendant unreacted chloromethyl groups in the final hypercrosslinked polymer, the largest portion, if not the majority of the groups, are located on the surface of the bead (or on the surface of large pores). This circumstance makes it possible to predominantly modify the surface of the polymer beads by involving the above chloromethyl groups into various chemical reactions that allow attachment of biocompatible and hemocompatible monomers, and/or cross-linkers or low molecular weight oligomers. The subsequent introduction of the sulfonic acid groups in the already formed network forms a sulfonic acid salt inner core (ion exchange resin) and a hemocompatible outer hydrogel exterior. Suitable choice of the reaction conditions for the sulfonation allows preservation or expression (via a protecting group) of the hemocompatible nature of the exterior hydrogel.

In yet another embodiment, the radical polymerization initiator is initially added to the dispersed organic phase, not the aqueous dispersion medium as is typical in suspension polymerization. During polymerization, many growing polymer chains with their chain-end radicals show up at the phase interface and can initiate the polymerization in the dispersion medium. Moreover, the radical initiator, like benzoyl peroxide, generates radicals relatively slowly. This initiator is only partially consumed during the formation of beads even after several hours of polymerization. This initiator easily moves toward the surface of the bead and activates the surface exposed pendant vinyl groups of the divinylbenzene moiety of the bead, thus initiating the graft: polymerization of other monomers added after the reaction has proceeded for a period of time. Therefore, free-radical grafting can occur during the transformation of the monomer droplets into polymer beads thereby incorporating monomers and/or cross-linkers or low molecular weight oligomers that impart biocompatibility or hemocompatibility as a surface coating. The subsequent introduction of the sulfonic acid groups in the already formed network forms a sulfonic acid salt inner core (ion exchange resin) and a hemocompatible outer hydrogel exterior. Suitable choice of the reaction conditions for the sulfonation allows preservation or expression (via a protecting group) of the hemocompatible nature of the exterior hydrogel.

In still yet another embodiment, hypercrosslinked or macroreticular porous polymer beads (including commercial versions) that have been sulfonated under mild conditions that retain residual functionality such as unreacted double bonds or chloromethyl groups can be modified via free radical or $S_N2$ type chemistry which would allow attachment of biocompatible and a hemocompatible monomers, and/or cross-linkers or low molecular weight oligomers. Among various "mild" sulfonating agents, Acetyl Sulfate (prepared from 98% conc. Sulfuric acid and acetic anhydride at low temperatures) is known to be very efficient for DVB or Styrene based polymeric materials. Sulfonation is usually done at 50° C. for several hours using equimolar amounts of acetyl sulfate and DVB or styrene based polymers. Sulfonation occurs mainly at the benzene ring and unreacted double bonds (in DVB based cross-linked polymeric porous beads) would be preserved for further functionalization. Usually after sulfonation with acetyl sulfate, the polymer is converted into —$SO_3Na$ form and can be graft copolymerized with N-vinyl pyrrolidone or other hemocompatible monomers and/or cross-linkers or low molecular weight oligomers (in bulk with benzoyl peroxide as initiator) or in water solutions (using sodium persulfate initiator). Resulting sulfonated polymer is "coated" with poly(N-vinylpyrrolidone), as an example, to create a hemocompatible material capable of removing $K^+$ cations from physiological fluids.

Some embodiments of the invention involve direct synthesis of porous polymeric beads containing —$SO_3Na$ groups. Any polymerizable vinyl monomer containing —$SO_3Na$ (or —$SO_3H$) groups can be polymerized in the presence of cross-linker monomer (like DVB, bis-acrylamide, bis-(meth)acrylates, etc.) and suitable porogen to yield porous polymeric beads containing above mentioned functionalities (—$SO_3Na$ or $SO_3H$). Vinyl monomers containing $SO_3Na$ or $SO_3H$ groups can also be copolymerized with hemocompatible monomer (NVP. 2-HEMA, etc.) in presence of porogen to yield hemocompatible porous beads containing —$SO_3Na$ groups.

Another embodiment of the invention involves making porous polymer beads containing $SO_3Na$ groups via graft copolymerization of premade porous polymers (containing double bonds unreacted) with polymerizable vinyl monomers containing —$SO_3Na$ or —$SO_3H$ groups (with the mixture of suitable hemocompatible vinyl monomers). Such monomers can be vinyl sulfonic acid Na salt, 4-styrene sulfonic acid Na salt, etc.

The hemoperfusion and perfusion devices consist of a packed bead bed of the porous polymer beads in a flow-through container fitted with either a retainer screen at both the exit end and the entrance end to maintain the bead bed inside the container or with a subsequent retainer screen to collect the beads after mixing. The hemoperfusion and perfusion operations are performed by passing the whole blood, blood plasma or physiologic fluid through the packed bead bed. During the perfusion through the bead bed, the toxic molecules are retained by sorption, torturous path, and/or ion exchange mechanism the while the remainder of the fluid and intact cell components pass through essentially unchanged in concentration.

In some other embodiments, an in-line filter is comprised of a packed bead bed of the porous polymer beads in a flow-through container, fitted with a retainer screen at both the exit end and the entrance end to maintain the bead bed inside the container. pRBCs are passed from a storage bag once-through the packed bead bed via gravity, during which the toxic molecules are retained by sorption, torturous path, and/or ion exchange mechanisms, while the remainder of the fluid and intact cell components pass through essentially unchanged in concentration.

Certain polymers useful in the invention (as is or after further modification) are macroporous polymers prepared from the polymerizable monomers of styrene, divinylbenzene, ethylvinylbenzene, and the acrylate and methacrylate monomers such as those listed below by manufacturer. Rohm and Haas Company, (now part of Dow Chemical Company): macroporous polymeric sorbents such as Amberlite™ XAD-1, Amberlite™ XAD-2, Amberlite™ XAD-4, Amberlite™ XAD-7, Amberlite™ XAD-7HP, Amberlite™ XAD-8, Amberlite™ XAD-16, Amberlite™ XAD-16 HP, Amberlite™ XAD-18, Amberlite™ XAD-200, Amberlite™ XAD-1180, Amberlite™ XAD-2000, Amberlite™ XAD-2005, Amberlite™ XAD-2010, Amberlite™ XAD-761, and Amberlite™ XE-305, and chromatographic grade sorbents such as Amberchrom™ CG 71, s,m,c, Amberchrom™ CG 161, s,m,c, Amberchrom™ CG 300, s,m,c, and Amberchrom™ CG 1000, s,m,c. Dow Chemical Company: Dowex™ Optipore™ L-493, Dowex™ Optipore™ V-493, Dowex™ Optipore™ V-502, Dowex™ Optipore™ L-285, Dowex™ Optipore™ L-323, and Dowex™ Optipore™ V-503. Lanxess (formerly Bayer and Sybron): Lewatit™ VPOC 1064 MD PH, Lewatit™ VPOC 1163, Lewatit™ OC EP 63, Lewatit™ S 6328A, Lewatit™ OC 1066, and Lewatit™ 60/150 MIBK. Mitsubishi Chemical Corporation: Diaion™ HP 10, Diaion™ HP 20, Diaion™ HP 21, Diaion™ HP 30, Diaion™ HP 40, Diaion™ HP 50, Diaion™ SP70, Diaion™ SP 205, Diaion™ SP 206, Diaion™ SP 207, Diaion™ SP 700, Diaion™ SP 800, Diaion™ SP 825, Diaion™ SP 850, Diaion™ SP 875, Diaion™ HP 1MG, Diaion™ HP 2MG, Diaion™ CHP 55A, Diaion™ CHP 55Y, Diaion™ CHP 20A, Diaion™ CHP 20Y, Diaion™ CHP 2MGY, Diaion™ CHP 20P, Diaion™ HP 20SS, Diaion™ SP 20SS, Diaion™ SP 207SS. Purolite Company: Purosorb™ AP 250 and Purosorb™ AP 400, and Kaneka Corp. Lixelle beads.

Various proteins may be adsorbed by the composition of the instant disclosure. Some of these proteins and their molecular weights are shown in the table below.

| Protein | Molecular Weight (Da) | Protein | Molecular Weight (Da) |
| --- | --- | --- | --- |
| PAF (Platelet Activating Factor) | 524 | Enterotoxin A, *S. aureus* | 27,800 |
| bilirubin | 548.6 | alpha toxin A&B, *S. aureus* | 28,000 |
| heme b | 616.5 | PCNA, proliferating cell nuclear antigen | 29,000 |
| MIP-1alpha | 8,000 | Arginse I | 35,000 |
| Complement C5a | 8,200 | Carboxypeptidase A | 35,000 |

-continued

| Protein | Molecular Weight (Da) | Protein | Molecular Weight (Da) |
|---|---|---|---|
| Complement C3a | 9,089 | Thrombin | 36,700 |
| IL-8 | 9,000 | alpha-1 antitrypsin | 44,324 |
| S100B (dimerizes) | 10,000 | TNF-alpha | 52,000 |
| β-2 microglobulin | 11,800 | Activated Protein C | 56,200 |
| Procalcitonin | 13,000 | Amylase | 57,000 |
| Phospholipase A2, secretory PLA2 type I pancreatic | 14,000 | hemopexin | 57,000 |
| PLA2G2A | 16,083 | alpha-1 antichymotrypsin | 55,000-68,000 |
| IL-7 | 17,400 | Diptheria toxoid | 62,000 |
| Myoglobin | 17,699 | hemoglobin, oxy | 64,000 |
| Trypsin-human pancreas | 23,300 | Pseudomonas Exotoxin A | 66,000 |
| IL-6 | 23,718 | ShigaToxin (A 32 kDa, 5 × B 7.7 kDa) | 69,000 |
| Toxic shock syndrome toxin 1 (TSST-1) | 24,000 | Calpain-1 (human erythrocytes) | 112,00 |
| Enterotoxin B, S aureus | 24,500 | C reactive Protein (5 × 25 kDa) | 115,000 |
| HMGB1 | 24,894 | Myeloperoxidase (neutrophils) | 150,000 |
| Interferon gamma | 25,000 | Immunoglobulin G IgG | 150,000 |
| Chymotrypsin | 25,000 | NOS synthase | 150,000 |
| Elastase (neutrophil) | 25,000 | Immunoglobulin A IgA | 162,000 |
| Trypsin | 26,488 | Immunoglobulin E (IgE) | 190,000 |
| PF4 | 27,100 | Immunoglobulin M IgM | 950,000 |

The following examples are intended to be exemplary and non-limiting.

EXAMPLE 1

Base Sorbent Synthesis CY12004, CY15042, CY15044, CY15045, and CY15077

The general description and the following detailed description are exemplary and explanatory only and are not restrictive of the invention, as defined in the appended claims. Other aspects of the present invention will be apparent to those skilled in the art in view of the detailed description of the invention as provided herein.

Reactor Setup; a 4-neck glass lid was affixed to a 3000 mL jacketed cylindrical glass reaction vessel using a stainless steel flange clamp and PFTE gasket. The lid was fitted with a PFTE stirrer bearing, RTD probe adapter, and water-cooled reflux condenser. A stainless steel stirring shaft having five 45° agitators was fit through the stirrer bearing and inserted into a digital overhead stirrer. An RTD probe was fit through the corresponding adapter, and connected to a PolyStat circulating heating and chilling unit. Compatible tubing was used to connect the inlet and outlet of the reaction vessel jacket to the appropriate ports on the Poly-Stat. The unused port in the lid was used for charging the reactor and was plugged at all other times.

Polymerization; Aqueous phase and organic phase compositions are shown below, in Table I and Table II, respectively. Ultrapure water was split into approximately equal parts in two separate Erlenmeyer flasks each containing a PFTE coated magnetic stir bar. Poly(vinyl alcohol) (PVA), having a degree of hydrolysis of 85.0 to 89.0 mol percent and a viscosity of 23.0 to 27.0 cP in a 4% aqueous solution at 20° C., was dispersed into the water in the first flask and heated to 80° C. on a hot plate with agitation. Salts (see Table 1, MSP, DSP, TSP and Sodium nitrite) were dispersed into the water in the second flask and heated to 80° C. on a hot plate with agitation. Circulation of heat transfer fluid from the PolyStat through the reaction vessel jacket was started, and fluid temperature heated to 60° C. Once PVA and salts dissolved, both solutions were charged to the reactor, one at a time, using a glass funnel. The digital overhead stirrer was powered on and the rpm set to a value to form appropriate droplet sizes upon organic phase addition. Temperature of the aqueous phase in the kettle was set to 70° C. The organic phase was prepared by adding benzoyl peroxide (BPO) to the divinylbenzene (DVB) and styrene in a 2 L Erlenmeyer flask and swirling until completely dissolved. 2,2,4-trimethylpentane and toluene were added to the flask, which was swirled to mix well. Once the temperature of the aqueous phase in the reactor reached 70° C., the organic phase was charged into the reactor using a narrow-necked glass funnel. Temperature of the reaction volume dropped upon the organic addition. A temperature program for the PolyStat was started, heating the reaction volume from 60 to 77° C. over 30 minutes, 77 to 80° C. over 30 minutes, holding the temperature at 80° C. for 960 minutes, and cooling to 20° C. over 60 minutes. 1-Vinyl-2-pyrrolidinone (VP) was added dropwise via glass separatory funnel once the reaction reached identity point, approximately one hour after the reaction temperature reached 80° C. Note: the temperature program for preparation of polymer CY15042 was different, proceeding as follows; reaction volume heated from 55 to 62° C. over 30 minutes, 62 to 65° C. over 30 minutes, held at 65° C. for 1320 minutes, heated from 65 to 82° C. over 30 minutes, 82 to 85° C. over 30 minutes, held at 85° C. for 60 minutes, then cooled to 20° C. over 60 minutes.

TABLE I

| Aqueous Phase Composition | |
|---|---|
| Reagent | Mass (g) |
| Ultrapure water | 1500.000 |
| Poly(vinyl alcohol) (PVA) | 4.448 |
| Monosodium phosphate (MSP) | 4.602 |
| Disodium phosphate (DSP) | 15.339 |
| Trisodium phosphate (TSP) | 9.510 |
| Sodium nitrite | 0.046 |
| Total | 1533.899 |

TABLE II

Organic Phase Compositions

| Reagent | CY12004 Mass (g) | CY15042 Mass (g) | CY15044 Mass (g) | CY15045 Mass (g) | CY15077 Mass (g) |
|---|---|---|---|---|---|
| Divinylbenzene, 63% (DVB) | 508.751 | 451.591 | 386.284 | 386.284 | 498.383 |
| Styrene | 0.000 | 0.00 | 374.118 | 374.118 | 0.000 |
| 2,2,4-trimethylpentane (Isooctane) | 384.815 | 125.800 | 271.210 | 271.210 | 482.745 |
| Toluene | 335.004 | 712.869 | 235.725 | 235.725 | 222.404 |
| Benzoyl peroxide, 98% (BPO) | 3.816 | 18.432 | 5.703 | 5.703 | 3.738 |
| 1-Vinyl-2-pyrrolidinone (VP) | 151.578 | 0.000 | 0.000 | 167.288 | 0.000 |
| Total (excluding BPO and VP) | 1228.571 | 1290.260 | 1267.337 | 1267.337 | 1203.532 |

The general description and the following detailed description are exemplary and explanatory only and are not restrictive of the invention, as defined in the appended claims. Other aspects of the present invention will be apparent to those skilled in the art in view of the detailed description of the invention as provided herein.

Work-up; reaction volume level in the reactor was marked. Overhead stirrer agitation was stopped, residual liquid siphoned out of the reactor, and the reactor filled to the mark with ultrapure water at room temperature. Overhead stirrer agitation was restarted and the slurry heated to 70° C. as quickly as possible. After 30 minutes, agitation was stopped and residual liquid siphoned out. Polymer beads were washed five times in this manner. During the final wash, the slurry temperature was cooled to room temperature. After the final water wash, polymer beads were washed with 99% isopropyl alcohol (IPA) in the same manner. 99% IPA was siphoned out and replaced with 70% IPA before transferring the slurry into a clean 4 L glass container. Unless noted otherwise, on an as-needed basis the polymer was steam stripped in a stainless steel tube for 8 hours, rewet in 70% IPA, transferred into DI water, sieved to obtain only the portion of beads having diameters between 300 and 600 µm, and dried at 100° C. until no further weight loss on drying was observed.

Cumulative pore volume data, measured by nitrogen desorption isotherm, for polymers CY12004, CY15042, CY15044, and CY15045, are presented below, in Tables III, IV, V, and VI, respectively. Cumulative pore volume data, measured by mercury intrusion porosimetry, for polymer CY15077 is presented in Table VII, below.

TABLE III

Nitrogen Desorption Data for CY12004

| Pore Diameter Range (Å) | Average Diameter (Å) | Cumulative Pore Volume (cm³/g) |
|---|---|---|
| 1221.6-868.1 | 985.2149834 | 0.009113091 |
| 868.1-751.9 | 801.4105771 | 0.019081821 |
| 751.9-661.5 | 700.749642 | 0.032021618 |
| 661.5-613.5 | 635.6650389 | 0.048206769 |
| 613.5-568.5 | 589.2088599 | 0.067981224 |
| 568.5-509.8 | 535.8385194 | 0.114704165 |
| 509.8-456.1 | 479.8625277 | 0.214714265 |
| 456.1-418.7 | 435.7117054 | 0.311269356 |
| 418.7-374.6 | 394.0534583 | 0.455991378 |
| 374.6-330.2 | 349.456374 | 0.579735461 |
| 330.2-319.6 | 324.7147611 | 0.612988132 |
| 319.6-281.8 | 298.1620033 | 0.708072633 |
| 281.8-273.9 | 277.7142728 | 0.73291244 |
| 273.9-256.6 | 264.6494358 | 0.777049805 |
| 256.6-237.0 | 245.9517985 | 0.830089884 |
| 237.0-225.7 | 231.0229263 | 0.857298007 |
| 225.7-215.6 | 220.375968 | 0.88145223 |

TABLE III-continued

Nitrogen Desorption Data for CY12004

| Pore Diameter Range (Å) | Average Diameter (Å) | Cumulative Pore Volume (cm³/g) |
|---|---|---|
| 215.6-145.5 | 166.3375231 | 1.066971104 |
| 145.5-104.6 | 117.8539174 | 1.181204175 |
| 104.6-84.4 | 92.0541661 | 1.241569291 |
| 84.4-71.4 | 76.67121175 | 1.285618005 |
| 71.4-60.9 | 65.20679768 | 1.326059561 |
| 60.9-52.7 | 56.07123392 | 1.360787093 |
| 52.7-46.5 | 49.12518253 | 1.389258246 |
| 46.5-41.3 | 43.53851295 | 1.416541075 |
| 41.3-37.1 | 38.91936166 | 1.445235862 |

TABLE IV

Nitrogen Desorption Data for CY15042

| Pore Diameter Range (Å) | Average Diameter (Å) | Cumulative Pore Volume (cm³/g) |
|---|---|---|
| 2011.0-633.1 | 751.380276 | 0.003621266 |
| 633.1-424.8 | 488.0919378 | 0.006317461 |
| 424.8-418.5 | 421.593936 | 0.006912678 |
| 418.5-353.5 | 380.29179 | 0.008267096 |
| 353.5-280.4 | 308.2300243 | 0.011094129 |
| 280.4-275.4 | 277.8814342 | 0.01168737 |
| 275.4-249.5 | 261.1230419 | 0.012721633 |
| 249.5-209.1 | 225.543664 | 0.015611261 |
| 209.1-206.8 | 207.9070897 | 0.016388077 |
| 206.8-137.5 | 157.790999 | 0.442556595 |
| 137.5-98.1 | 110.7933773 | 0.765560391 |
| 98.1-81.8 | 88.28728758 | 0.845836735 |
| 81.8-67.3 | 72.96250925 | 0.911182647 |
| 67.3-57.7 | 61.63744463 | 0.954008444 |
| 57.7-50.3 | 53.43111186 | 0.983515641 |
| 50.3-44.4 | 46.93705679 | 1.010486042 |
| 44.4-38.6 | 41.02620024 | 1.037817277 |
| 38.6-34.5 | 36.30857144 | 1.058861412 |
| 34.5-30.9 | 32.48566551 | 1.08400665 |
| 30.9-27.3 | 28.85395017 | 1.10131894 |
| 27.3-24.3 | 25.59611525 | 1.12576046 |
| 24.3-22.3 | 23.18199338 | 1.143118464 |
| 22.3-19.6 | 20.72009386 | 1.167009752 |
| 19.6-17.4 | 18.32182238 | 1.190109864 |

TABLE V

Nitrogen Desorption Data for CY15044

| Pore Diameter Range (Å) | Average Diameter (Å) | Cumulative Pore Volume (cm³/g) |
|---|---|---|
| 2529.6-789.0 | 936.1742201 | 1.75877E-06 |
| 789.0-446.0 | 526.203721 | 0.000135623 |
| 446.0-219.6 | 260.7379647 | 0.002068559 |

TABLE V-continued

Nitrogen Desorption Data for CY15044

| Pore Diameter Range (Å) | Average Diameter (Å) | Cumulative Pore Volume (cm³/g) |
| --- | --- | --- |
| 219.6-213.4 | 216.3756282 | 0.004663144 |
| 213.4-205.7 | 209.3598959 | 0.0088853 |
| 205.7-144.7 | 164.0510277 | 0.131650053 |
| 144.7-99.6 | 113.2793455 | 0.294709491 |
| 99.6-82.1 | 88.98089675 | 0.331539838 |
| 82.1-71.4 | 75.89033961 | 0.34527909 |
| 71.4-60.0 | 64.52630192 | 0.360216738 |
| 60.0-52.8 | 55.83732662 | 0.367929549 |
| 52.8-46.8 | 49.32751384 | 0.373710394 |
| 46.8-41.4 | 43.66300585 | 0.378313283 |
| 41.4-37.2 | 39.02724789 | 0.38481289 |
| 37.2-33.2 | 34.8920748 | 0.391803401 |
| 33.2-30.0 | 31.34913535 | 0.393761301 |
| 30.0-27.3 | 28.49102813 | 0.394422444 |
| 27.3-24.7 | 25.83440471 | 0.396180539 |
| 24.7-22.3 | 23.34690716 | 0.401510134 |
| 22.3-19.8 | 20.83368622 | 0.40782788 |
| 19.8-17.5 | 18.45917969 | 0.416568116 |

TABLE VI

Nitrogen Desorption Data for CY15045

| Pore Diameter Range (Å) | Average Diameter (Å) | Cumulative Pore Volume (cm³/g) |
| --- | --- | --- |
| 1277.7-542.6 | 649.560333 | 0.000489722 |
| 542.6-213.2 | 252.9981774 | 0.000667721 |
| 213.2-206.9 | 209.9696024 | 0.001419558 |
| 206.9-141.9 | 161.6476715 | 0.261729457 |
| 141.9-106.3 | 118.498425 | 0.346563251 |
| 106.3-84.0 | 92.17838423 | 0.37856771 |
| 84.0-71.8 | 76.76600632 | 0.393497452 |
| 71.8-62.4 | 66.31374327 | 0.404409264 |
| 62.4-53.6 | 57.17863111 | 0.411077722 |
| 53.6-48.0 | 50.38372676 | 0.416000386 |
| 48.0-42.5 | 44.81172299 | 0.421626585 |
| 42.5-38.3 | 40.08447096 | 0.428067208 |
| 38.3-34.4 | 36.07215077 | 0.431303175 |
| 34.4-31.5 | 32.76081107 | 0.433543649 |
| 31.5-26.3 | 27.29321095 | 0.440720595 |
| 26.3-23.8 | 24.89263623 | 0.44207166 |
| 23.8-21.3 | 22.31849785 | 0.443967237 |
| 21.3-19.1 | 19.99937462 | 0.45436982 |
| 19.1-16.1 | 17.16801839 | 0.47745598 |

TABLE VII

Mercury Intrusion Data for CY15077

| Pore size Diameter (A) | Cumulative Intrusion (mL/g) |
| --- | --- |
| 226299.0625 | 3.40136E−30 |
| 213166.0781 | 0.001678752 |
| 201295.1563 | 0.002518128 |
| 172635.8125 | 0.004364755 |
| 139538.0625 | 0.007554384 |
| 113120.7813 | 0.011919139 |
| 90542.36719 | 0.01645177 |
| 78733.25781 | 0.0203129 |
| 72446.375 | 0.022327403 |
| 60340.40234 | 0.027867284 |
| 48343.83984 | 0.035327822 |
| 39009.13672 | 0.040918175 |
| 32136.4082 | 0.04899035 |
| 25330.65625 | 0.063195683 |
| 20981.51563 | 0.079529688 |
| 16219.86426 | 0.108860672 |
| 13252.41211 | 0.141730919 |
| 10501.53613 | 0.193969816 |

TABLE VII-continued

Mercury Intrusion Data for CY15077

| Pore size Diameter (A) | Cumulative Intrusion (mL/g) |
| --- | --- |
| 8359.911133 | 0.262399256 |
| 6786.30127 | 0.345866203 |
| 5538.122559 | 0.438174427 |
| 4337.931152 | 0.563276172 |
| 3501.674805 | 0.681870878 |
| 2838.742188 | 0.804727197 |
| 2593.016846 | 0.865813017 |
| 2266.688965 | 0.938610673 |
| 1831.041748 | 1.056586146 |
| 1509.850708 | 1.163395643 |
| 1394.006104 | 1.21002543 |
| 1294.780151 | 1.257248282 |
| 1207.692627 | 1.293158531 |
| 1131.860962 | 1.326992273 |
| 1065.099976 | 1.35812819 |
| 953.1816406 | 1.405935764 |
| 884.0358887 | 1.445426106 |
| 823.5491333 | 1.478719592 |
| 770.9108276 | 1.510579824 |
| 722.4724731 | 1.537048101 |
| 684.6119995 | 1.564400196 |
| 672.187561 | 1.581117511 |
| 636.7885742 | 1.60271585 |
| 604.7248535 | 1.621845484 |
| 558.1287231 | 1.651492 |
| 518.2624512 | 1.678913713 |
| 483.5536499 | 1.708594561 |
| 453.5110779 | 1.735918999 |
| 426.9998474 | 1.755934 |
| 403.1251526 | 1.783603072 |
| 382.7776794 | 1.793849826 |
| 362.7162476 | 1.817784309 |
| 342.3734436 | 1.838774562 |
| 330.1105042 | 1.851493955 |
| 315.5238037 | 1.869742155 |
| 302.2973938 | 1.885128617 |
| 290.2946777 | 1.895119786 |
| 279.1246643 | 1.912378907 |
| 268.7442627 | 1.924305081 |
| 259.1106873 | 1.936048627 |
| 241.8737793 | 1.955100656 |
| 226.7678223 | 1.972970247 |
| 213.3626251 | 1.988123298 |
| 201.4908142 | 2.007521152 |
| 194.9888611 | 2.022114754 |
| 188.9506989 | 2.033871174 |
| 180.582901 | 2.035052776 |
| 172.8530121 | 2.050720692 |
| 164.9621735 | 2.062945843 |
| 157.8110657 | 2.071056128 |
| 151.1540375 | 2.082133055 |
| 143.9185333 | 2.096480608 |
| 138.4670563 | 2.106938839 |
| 132.8492737 | 2.119287968 |
| 129.5760345 | 2.126605988 |
| 126.5438614 | 2.126605988 |
| 124.2635574 | 2.132267475 |
| 120.8976135 | 2.141504765 |
| 117.3792267 | 2.150759459 |
| 114.791893 | 2.154810667 |
| 111.9475937 | 2.162935257 |
| 108.8830032 | 2.167646885 |
| 106.6480179 | 2.174062729 |
| 104.5217743 | 2.179908991 |
| 102.4295197 | 2.179908991 |
| 100.1580353 | 2.182951927 |
| 98.29322052 | 2.184018135 |
| 96.44822693 | 2.191127539 |
| 94.42159271 | 2.198545218 |
| 91.52587891 | 2.209161043 |
| 89.25807953 | 2.209312439 |
| 87.0777359 | 2.215425491 |
| 85.42358398 | 2.221472025 |
| 83.62612915 | 2.232139587 |
| 82.11174011 | 2.237514496 |
| 79.91614532 | 2.239231586 |

TABLE VII-continued

Mercury Intrusion Data for CY15077

| Pore size Diameter (A) | Cumulative Intrusion (mL/g) |
| --- | --- |
| 78.01462555 | 2.239560127 |
| 76.19993591 | 2.239560127 |
| 75.09249115 | 2.239560127 |
| 73.41201019 | 2.239560127 |
| 72.23709869 | 2.240245819 |
| 71.09960175 | 2.242422104 |
| 69.86301422 | 2.243849993 |
| 68.40761566 | 2.257676363 |
| 67.13697815 | 2.259181261 |
| 66.03359222 | 2.266284466 |
| 65.08189392 | 2.270181179 |
| 64.04368591 | 2.272682428 |
| 62.38490295 | 2.280714512 |
| 61.32764053 | 2.280714512 |
| 60.30379868 | 2.287917852 |
| 59.41370392 | 2.287917852 |
| 58.54679489 | 2.293802738 |
| 57.79866409 | 2.297607183 |
| 56.88977814 | 2.299046278 |
| 55.9213295 | 2.302111387 |
| 54.98665237 | 2.303381443 |

EXAMPLE 2

Polymer Modification CY15087

The general description and the following detailed description are exemplary and explanatory only and are not restrictive of the invention, as defined in the appended claims. Other aspects of the present invention will be apparent to those skilled in the art in view of the detailed description of the invention as provided herein.

N-vinylpyrrolidone functionalization; base polymer, CY15077, was not steam stripped or sieved prior to functionalization. Two 99% IPA washes at 50° C. were completed during workup for the base polymer, as opposed to one wash at RT. Following IPA washes, the polymer was washed three times with an excess of DI water. Wetted CY15077 polymer beads were added to a 1 L jacketed glass reaction kettle, fitted with a Teflon coated agitator, containing 450 mL DI water, 50.0 g N-vinylpyrrolidone monomer, and 1.5 g sodium persulfate. The reaction was allowed to proceed for 24 hours at 75° C., with agitation speed set to 100 RPM. Upon completion the polymer beads were washed five times with 500 mL DI water at 70° C., steam stripped in a stainless steel tube for 8 hours, rewet in 70% IPA, transferred into DI water, sieved to obtain only the portion of beads having diameters between 300 and 600 μm, and dried at 100° C. until no further weight loss on drying was observed. The yield was 95.5 g of polymer CY15087. Atomic concentrations measured by XPS, and cumulative pore volume data measured by mercury intrusion porosimetry, are shown in Tables VIII and IX, respectively.

TABLE VIII

Atomic Concentrations (in %) for CY15077 and CY15087

| Polymer | Condition | C | N | O |
| --- | --- | --- | --- | --- |
| CY15077 | Bead | 96.2 | 0.0 | 3.8 |
| CY15077 | Ground | 98.6 | 0.0 | 1.4 |
| CY15087 | Bead | 95.5 | 0.4 | 4.2 |
| CY15087 | Ground | 98.3 | 0.2 | 1.5 |

TABLE IX

Mercury Intrusion Data for CY15087

| Pore size Diameter (A) | Cumulative Intrusion (mL/g) |
| --- | --- |
| 226275.6875 | 3.003E−30 |
| 213126.625 | 0.001333927 |
| 201250.5938 | 0.002964283 |
| 172601.8438 | 0.005928566 |
| 139532.5469 | 0.009189277 |
| 113124.3359 | 0.012449989 |
| 90545.25 | 0.015710698 |
| 78739.35156 | 0.017489269 |
| 72432.5625 | 0.01897141 |
| 60333.77734 | 0.021935694 |
| 46762.60547 | 0.026795639 |
| 39173.96094 | 0.03074207 |
| 31808.34375 | 0.034442116 |
| 25357.64648 | 0.040027067 |
| 20929.94141 | 0.046409778 |
| 16182.15234 | 0.056623131 |
| 13255.21973 | 0.065796889 |
| 10561.28809 | 0.080750667 |
| 8353.926758 | 0.105692402 |
| 6778.929199 | 0.138670683 |
| 5543.002441 | 0.177410021 |
| 4342.263672 | 0.24024339 |
| 3502.678711 | 0.308058321 |
| 2839.226807 | 0.388105094 |
| 2591.51416 | 0.428066701 |
| 2267.699951 | 0.48154822 |
| 1831.208252 | 0.570007741 |
| 1510.12561 | 0.655585647 |
| 1394.226563 | 0.696180701 |
| 1294.746582 | 0.729135811 |
| 1208.07251 | 0.76245892 |
| 1132.023804 | 0.795990944 |
| 1065.684937 | 0.815372229 |
| 953.989502 | 0.855566621 |
| 883.8703613 | 0.871785223 |
| 823.4996338 | 0.921781898 |
| 771.3513794 | 0.949763238 |
| 722.1901207 | 1.018806458 |
| 684.8914185 | 1.027466536 |
| 671.8579712 | 1.033001781 |
| 636.456604 | 1.044957519 |
| 604.6593018 | 1.05753231 |
| 557.9059448 | 1.079107881 |
| 518.4785156 | 1.102458835 |
| 483.8456726 | 1.127018452 |
| 453.9489746 | 1.151340365 |
| 426.8711243 | 1.174746156 |
| 402.8918152 | 1.194709539 |
| 382.4490967 | 1.213674426 |
| 360.680481 | 1.231868267 |
| 342.5672302 | 1.252067924 |
| 329.8339539 | 1.267953753 |
| 315.4637756 | 1.28668797 |
| 302.4020996 | 1.299176812 |
| 290.331665 | 1.314114213 |
| 279.2361145 | 1.322446585 |
| 268.7993164 | 1.34148562 |
| 259.2027283 | 1.349915743 |
| 241.8540192 | 1.363333344 |
| 226.7354431 | 1.38415575 |
| 213.408844 | 1.386666298 |
| 201.5056763 | 1.411639214 |
| 194.9947357 | 1.426415801 |
| 188.935318 | 1.428328514 |
| 180.6179199 | 1.441128492 |
| 172.8575745 | 1.453100324 |
| 164.9869385 | 1.464205742 |
| 157.740097 | 1.473819733 |
| 151.1829987 | 1.486423731 |
| 143.9502716 | 1.499343991 |
| 138.4791107 | 1.509965897 |
| 132.8890839 | 1.522242427 |
| 129.5950317 | 1.529255748 |
| 126.493248 | 1.529255748 |
| 124.2660522 | 1.53686142 |
| 120.8921432 | 1.543375134 |

TABLE IX-continued

Mercury Intrusion Data for CY15087

| Pore size Diameter (A) | Cumulative Intrusion (mL/g) |
|---|---|
| 117.3944702 | 1.549948096 |
| 114.7864304 | 1.558065772 |
| 111.9504318 | 1.56092155 |
| 108.9145203 | 1.564850807 |
| 106.6669846 | 1.571887255 |
| 104.5330276 | 1.574593782 |
| 102.4421844 | 1.584572434 |
| 100.1668015 | 1.591516852 |
| 98.28172302 | 1.594149351 |
| 96.44982147 | 1.595042825 |
| 94.43471527 | 1.595328212 |
| 91.55084229 | 1.595610261 |
| 89.27562714 | 1.604250789 |
| 87.08631134 | 1.61047101 |
| 85.43348694 | 1.616541862 |
| 83.63105011 | 1.620805621 |
| 82.10086823 | 1.627643347 |
| 79.91345978 | 1.629765868 |
| 78.01348877 | 1.631207824 |
| 76.20350647 | 1.63190341 |
| 75.09172821 | 1.634262919 |
| 73.41147614 | 1.638391137 |
| 72.23751831 | 1.642881751 |
| 71.10028076 | 1.646320224 |
| 69.861763 | 1.648736954 |
| 68.40744019 | 1.655003667 |
| 67.13788605 | 1.662294388 |
| 66.03204346 | 1.667405605 |
| 65.08184814 | 1.670548201 |
| 64.04498291 | 1.671463728 |
| 62.38602829 | 1.673002481 |
| 61.32709885 | 1.673002481 |
| 60.30479813 | 1.673002481 |
| 59.41309738 | 1.673002481 |
| 58.54596329 | 1.673002481 |
| 57.799366 | 1.673613429 |
| 56.88968277 | 1.673613429 |
| 55.92052078 | 1.677541733 |
| 54.98633194 | 1.677541733 |

EXAMPLE 3

Polymer Modification CY15100 and CY15102

The general description and the following detailed description are exemplary and explanatory only and are not restrictive of the invention, as defined in the appended claims. Other aspects of the present invention will be apparent to those skilled in the art in view of the detailed description of the invention as provided herein.

Sulfonation procedure; dried base polymer was added to a 1 L jacketed glass reactor, which was equipped with a Teflon coated agitator. A mixture of concentrated sulfuric acid (98%) and fuming sulfuric acid (20% $SO_3$ in sulfuric acid) was added to the reactor containing base polymer. The reaction was carried out at 90° C. for 24 hours, with constant agitation at 100 RPM.

Work-up; the reaction volume was allowed to cool to room temperature (RT), and was slowly added into a chemical glass beaker with an excess of at least 1 L ice cold DI water. Sulfonated polymer was washed with excess DI water at RT until the supernatant reached a neutral pH. The resulting polymer was then treated with 100 mL 1 M $NaOH_{(aq)}$ for 1 hour at RT to convert polymer bound $\sim SO_3H$ into $\sim SO_3Na$ groups. Polymer was washed again with an excess of DI water at RT until the supernatant reached a neutral pH, then dried in an oven at 100° C. until no further loss on drying was observed. The dried $\sim SO_3Na$ functional polymer yield was measured. Reaction compositions for CY15100 and CY15102 are provided in Table X. Table XI displays atomic concentrations for polymers CY15100, CY15102, and CY15087, as measured by XPS. Log differential pore volume plots are presented in FIGS. 1, 2, and 3, and cumulative pore volume data are presented in Tables XII, XIII, and XIV. When interpreting pore structure data obtained from nitrogen desorption isotherm or mercury intrusion porosimetry using dried polymer as the sample, it is important to consider that pore size may change upon swelling of sulfonated poly(styrene-co-divinylbenzene) porous beads once wetted in solution. In addition to potential changes in pore structure, the bead size may also change upon transition from dry to swollen state. This phenomenon was evaluated in "Preparation and Evaluation of Differently Sulfonated Styrene-Divinylbenzene Cross-Linked Copolymer Cationic Exchange Resins as Novel Carriers for Drug Delivery", published in AAPS PharmSciTech June 2009; 10 (2): 641-648.

Thrombogenicity was measured by the uPTT assay in which materials were compared to the negative control (plasma alone), positive control (glass beads) and reference beads to determine the degree of contact activation activity. In the uPTT assay, the % change in clot formation over time as compared to the reference materials was determined, then grouped according to: <25% activators, 25-49% moderate activators, 50-74% mild activators, 75-100% minimal and >100% non-activators of the intrinsic coagulation pathway. Polymer CY15100, 82%, was a minimal activator.

TABLE X

Modification Compositions for CY15100 and CY15102

|  | CY15100 | CY15102 |
|---|---|---|
| Base Polymer | CY15045 | CY15087 |
| Mass Base Polymer (g) | 220.0 | 80.0 |
| Mass Concentrated Sulfuric Acid (g) | 950.0 | 550.0 |
| Mass Fuming Sulfuric Acid (g) | 50.0 | 30.0 |
| Yield Dry Modified Polymer (g) | 355.5 | 204.6 |

TABLE XI

Atomic Concentrations (in %) for CY15100, CY15102, and CY15087

| Polymer | Condition | C | N | O | Na | S |
|---|---|---|---|---|---|---|
| CY15100 | Bead | 65.7 | 0.2 | 20.5 | 8.0 | 5.7 |
| CY15102 | Bead | 71.6 | 0.5 | 17.2 | 6.6 | 4.1 |
| CY15087 | Bead | 95.5 | 0.4 | 4.2 | 0.0 | 0.0 |
| CY15087 | Ground | 98.3 | 0.2 | 1.5 | 0.0 | 0.0 |

TABLE XII

Nitrogen Desorption Data for CY15100

| Pore Diameter Range (Å) | Average Diameter (Å) | Cumulative Pore Volume (cm³/g) |
|---|---|---|
| 2072.6-552.5 | 648.562383 | 0.000416099 |
| 552.5-354.3 | 410.9223564 | 0.000905416 |
| 354.3-337.5 | 345.4980521 | 0.001122701 |
| 337.5-311.7 | 323.5292132 | 0.001561729 |
| 311.7-288.8 | 299.3515093 | 0.001919004 |
| 288.8-272.0 | 279.8911375 | 0.002345465 |
| 272.0-252.4 | 261.4265539 | 0.002783018 |
| 252.4-239.0 | 245.303922 | 0.003244227 |
| 239.0-225.7 | 231.9701343 | 0.004052829 |

TABLE XII-continued

Nitrogen Desorption Data for CY15100

| Pore Diameter Range (Å) | Average Diameter (Å) | Cumulative Pore Volume (cm³/g) |
|---|---|---|
| 225.7-212.7 | 218.7962082 | 0.005280802 |
| 212.7-204.5 | 208.4059706 | 0.007418375 |
| 204.5-131.6 | 152.2941936 | 0.087124009 |
| 131.6-99.3 | 110.8101833 | 0.170472908 |
| 99.3-72.3 | 81.43320551 | 0.20555251 |
| 72.3-62.2 | 66.46726774 | 0.212857437 |
| 62.2-52.1 | 56.21812708 | 0.218554756 |
| 52.1-45.7 | 48.42881742 | 0.221509707 |
| 45.7-39.4 | 42.03869424 | 0.223879096 |
| 39.4-34.5 | 36.58507436 | 0.225521077 |
| 34.5-29.1 | 31.32500867 | 0.230015257 |
| 29.1-25.1 | 26.83485239 | 0.230195589 |
| 25.1-22.0 | 23.36857621 | 0.230286279 |
| 22.0-19.4 | 20.51213112 | 0.232863812 |

TABLE XIII

Nitrogen Desorption Data for CY15102

| Pore Diameter Range (Å) | Average Diameter (Å) | Cumulative Pore Volume (cm³/g) |
|---|---|---|
| 1598.8-1238.8 | 1372.941344 | 0.026272341 |
| 1238.8-946.4 | 1053.220361 | 0.092081573 |
| 946.4-758.1 | 831.0482586 | 0.194131921 |
| 758.1-677.1 | 712.8857859 | 0.258283006 |
| 677.1-529.4 | 584.7345957 | 0.38744334 |
| 529.4-485.2 | 505.2928332 | 0.431560876 |
| 485.2-443.2 | 462.211297 | 0.481712669 |
| 443.2-396.6 | 417.205311 | 0.529431372 |
| 396.6-361.7 | 377.5005059 | 0.571368548 |
| 361.7-324.6 | 341.0804153 | 0.616836751 |
| 324.6-296.1 | 308.9881056 | 0.653318693 |
| 296.1-271.6 | 282.7268533 | 0.684779469 |
| 271.6-256.8 | 263.7792955 | 0.704908544 |
| 256.8-239.4 | 247.4475287 | 0.727833901 |
| 239.4-230.2 | 234.5702219 | 0.739926683 |
| 230.2-217.1 | 223.2037828 | 0.756372211 |
| 217.1-206.8 | 211.680438 | 0.769442061 |
| 206.8-140.7 | 160.5985991 | 0.863794835 |
| 140.7-106.0 | 118.0466801 | 0.922556622 |
| 106.0-82.8 | 91.24150017 | 0.968039661 |
| 82.8-68.2 | 73.90381313 | 1.001829887 |
| 68.2-60.9 | 64.05281388 | 1.020920023 |
| 60.9-52.5 | 55.98109194 | 1.044868856 |
| 52.5-46.3 | 48.94597942 | 1.065247397 |
| 46.3-41.2 | 43.35983259 | 1.084233305 |
| 41.2-37.0 | 38.81504369 | 1.106456908 |
| 37.0-33.1 | 34.78421912 | 1.129603729 |
| 33.1-30.0 | 31.33519542 | 1.146218801 |
| 30.0-27.3 | 28.4688972 | 1.162517069 |
| 27.3-24.6 | 25.75215358 | 1.182048628 |
| 24.6-22.4 | 23.33791231 | 1.201310022 |
| 22.4-19.8 | 20.89212489 | 1.229148706 |
| 19.8-17.6 | 18.54892595 | 1.260822457 |

TABLE XIV

Mercury Intrusion Data for CY15102

| Pore size Diameter (A) | Cumulative Intrusion (mL/g) |
|---|---|
| 226247.25 | 3.02E-30 |
| 213156.0625 | 0.000893837 |
| 201297.1875 | 0.002383566 |
| 172619.2656 | 0.004320214 |
| 139526.7344 | 0.006107889 |
| 113150.6484 | 0.007448644 |
| 90544.85156 | 0.009236319 |
| 78737.24219 | 0.010130156 |
| 72447.07031 | 0.011172966 |
| 60339.52344 | 0.012066803 |
| 49074.61719 | 0.012066803 |
| 38783.65625 | 0.012066803 |
| 32031.35742 | 0.012456137 |
| 25154.1582 | 0.01550037 |
| 20919.94336 | 0.01550037 |
| 16226.36035 | 0.016433783 |
| 13231.0293 | 0.018065026 |
| 10569.24219 | 0.020413134 |
| 8346.358398 | 0.023545867 |
| 6777.795898 | 0.027556093 |
| 5545.635742 | 0.032167129 |
| 4347.45166 | 0.039555997 |
| 3496.898926 | 0.049277436 |
| 2839.973145 | 0.057190847 |
| 2592.47998 | 0.06178461 |
| 2267.395264 | 0.071647309 |
| 1831.758789 | 0.089788206 |
| 1510.39563 | 0.112907536 |
| 1394.068237 | 0.125744253 |
| 1294.699707 | 0.136810422 |
| 1207.551147 | 0.147966579 |
| 1132.260498 | 0.159586608 |
| 1065.672974 | 0.171025708 |
| 954.0095215 | 0.191800222 |
| 884.2581177 | 0.20811981 |
| 823.8370972 | 0.228217274 |
| 771.1380615 | 0.239915013 |
| 721.8734131 | 0.275565475 |
| 684.4716797 | 0.281177133 |
| 672.791748 | 0.283745468 |
| 636.3512573 | 0.295114249 |
| 605.4035034 | 0.309263676 |
| 558.758606 | 0.326112717 |
| 518.5050049 | 0.352752388 |
| 483.7310181 | 0.367008656 |
| 453.6919861 | 0.390547335 |
| 426.9628296 | 0.407471895 |
| 403.0959778 | 0.4232741 |
| 382.8546753 | 0.444355428 |
| 362.905426 | 0.463873088 |
| 342.0473328 | 0.487040371 |
| 329.7276001 | 0.504495382 |
| 315.7310791 | 0.522837102 |
| 302.3917236 | 0.545027971 |
| 290.2372131 | 0.567096949 |
| 279.1113586 | 0.588691056 |
| 268.6489563 | 0.608853817 |
| 259.2150879 | 0.635331511 |
| 241.9123993 | 0.710671127 |
| 226.7029877 | 0.774290979 |
| 213.3559113 | 0.867704988 |
| 201.5307922 | 0.867704988 |
| 195.0246887 | 0.867704988 |
| 188.9438019 | 0.867704988 |
| 180.6033783 | 0.867704988 |
| 172.8410034 | 0.869671643 |
| 164.969101 | 0.869671643 |
| 157.8126526 | 0.87475878 |
| 151.1803131 | 0.905465066 |
| 143.936264 | 0.909094393 |
| 138.4554596 | 0.931292474 |
| 132.8584442 | 0.938616037 |
| 129.575531 | 0.938616037 |
| 126.4766693 | 0.971493781 |
| 124.2657852 | 0.971493781 |
| 120.9015427 | 0.972762465 |
| 117.374855 | 0.977469385 |
| 114.7828751 | 0.981295645 |
| 111.9444351 | 0.981295645 |
| 108.8816452 | 0.981295645 |
| 106.6592331 | 0.986702561 |
| 104.5428238 | 0.996097863 |
| 102.4358368 | 1.000003457 |
| 100.1722946 | 1.003374338 |

TABLE XIV-continued

Mercury Intrusion Data for CY15102

| Pore size Diameter (A) | Cumulative Intrusion (mL/g) |
|---|---|
| 98.26839447 | 1.006461024 |
| 96.44637299 | 1.008966684 |
| 94.41146851 | 1.012030125 |
| 91.54938507 | 1.015347958 |
| 89.25726318 | 1.018440247 |
| 87.0788269 | 1.021567345 |
| 85.42123413 | 1.024644852 |
| 83.62944031 | 1.028239489 |
| 82.1011734 | 1.02980864 |
| 79.91355133 | 1.032312155 |
| 78.00926208 | 1.034948707 |
| 76.20082092 | 1.037501097 |
| 75.09120178 | 1.039880157 |
| 73.4092865 | 1.042042732 |
| 72.23842621 | 1.043176413 |
| 71.09993744 | 1.047091961 |
| 69.86208344 | 1.047258615 |
| 68.40840912 | 1.049208641 |
| 67.1362381 | 1.05278945 |
| 66.0329895 | 1.05278945 |
| 65.08166504 | 1.053350925 |
| 64.04417419 | 1.054639339 |
| 62.38519287 | 1.055902362 |
| 61.32834625 | 1.060090899 |
| 60.30381012 | 1.062460899 |
| 59.41312408 | 1.063420892 |
| 58.54793549 | 1.064275384 |
| 57.79902267 | 1.066532493 |
| 56.88972473 | 1.068112493 |
| 55.92105865 | 1.072528958 |
| 54.9865036 | 1.072528958 |

EXAMPLE 4

Polymer Modification CY14144 and CY15101

The general description and the following detailed description are exemplary and explanatory only and are not restrictive of the invention, as defined in the appended claims. Other aspects of the present invention will be apparent to those skilled in the art in view of the detailed description of the invention as provided herein.

Sulfonation procedure; dried base polymer was mixed with glacial acetic acid in a 500 mL glass reactor equipped with a Teflon coated mechanical agitator, and heated to 50° C. with agitation set to 100 RPM. A mild sulfonating agent was prepared by adding acetic anhydride (99%) to a 100 mL chemical glass beaker, cooled in an ice bath, and slowly adding concentrated sulfuric acid (98%) over 30 minutes. Temperature of the mixture was monitored and maintained between 15-40° C. by replenishing the ice bath. After completion of the sulfuric acid addition, the reddish-brown viscous liquid was kept at RT for 1 hour, and then slowly added to the reactor. The reaction was allowed to proceed for a specified amount of time.

Work-up; the reaction volume was allowed to cool to room temperature (RT), and was slowly added into a chemical glass beaker with an excess of at least 1 L ice cold DI water. Sulfonated polymer was washed with excess DI water at RT until the supernatant reached a neutral pH. The resulting polymer was then treated with 100 mL 1M $NaOH_{(aq)}$ for 1 hour at RT to convert polymer bound $\sim SO_3H$ into $\sim SO_3Na$ groups. Polymer was washed again with an excess of DI water at RT until the supernatant reached a neutral pH, then dried in an oven at 100° C. until no further loss on drying was observed. The dried $\sim SO_3Na$ functional polymer yield was measured. Reaction compositions for polymers CY14144 and CY15101 are shown in Table XV, below. Atomic concentrations determined by XPS for polymers CY14144, CY12004, CY15101, and CY15087 are presented below, in Table XVI. FIGS. 4, 5, and 6 show plots of log differential pore volume for each of the modified polymers described above. Cumulative pore volume data are shown below in Tables XVII, XVIII, and XIX.

Thrombogenicity was measured by the uPTT assay in which materials were compared to the negative control (plasma alone), positive control (glass beads) and reference beads to determine the degree of contact activation activity. In the uPTT assay, the % change in clot formation over time as compared to the reference materials was determined, then grouped according to: <25% activators, 25-49% moderate activators, 50-74% mild activators, 75-100% minimal and >100% non-activators of the intrinsic coagulation pathway. Polymer CY15101, 88%, was a minimal activator.

TABLE XV

Modification Compositions for CY14144 and CY15101

|  | CY14144 | CY15101 |
|---|---|---|
| Base Polymer | CY12004 | CY15087 |
| Mass Base Polymer (g) | 11.7 | 80.5 |
| Volume Glacial Acetic Acid (mL) | 75 | 400 |
| Mass Acetic Anhydride (g) | 15.5 | 125.0 |
| Mass Concentrated Sulfuric Acid (g) | 10.0 | 80.0 |
| Reaction Time (hr) | 1 | 2 |
| Yield Dry Modified Polymer (g) | 15.2 | 103.4 |

TABLE XVI

Atomic Concentrations (in %) for CY14144, CY12004, CY15101 and CY15087

| Polymer | Condition | C | N | O | Na | S |
|---|---|---|---|---|---|---|
| CY14144 | Ground | 87.0 | 0.0 | 8.7 | 2.5 | 1.8 |
| CY12004 | Bead | 88.7 | 3.4 | 7.9 | 0.0 | 0.0 |
| CY12004 | Ground | 95.0 | 0.4 | 4.7 | 0.0 | 0.0 |
| CY15101 | Bead | 93.3 | 0.7 | 5.5 | 0.4 | 0.1 |
| CY15087 | Bead | 95.5 | 0.4 | 4.2 | 0.0 | 0.0 |
| CY15087 | Ground | 98.3 | 0.2 | 1.5 | 0.0 | 0.0 |

TABLE XVII

Nitrogen Desorption Data for CY14144

| Pore Diameter Range (Å) | Average Diameter (Å) | Cumulative Pore Volume (cm³/g) |
|---|---|---|
| 1316.7-872.8 | 1006.357045 | 0.00765904 |
| 872.8-760.0 | 808.4322272 | 0.01624896 |
| 760.0-683.5 | 717.5974884 | 0.028034508 |
| 683.5-625.7 | 651.9899544 | 0.04390322 |
| 625.7-580.4 | 601.3250683 | 0.063539075 |
| 580.4-506.1 | 537.9818896 | 0.171853178 |
| 506.1-449.5 | 474.3191955 | 0.315569993 |
| 449.5-395.6 | 418.9973346 | 0.494055963 |
| 395.6-367.4 | 380.4061561 | 0.562885137 |
| 367.4-336.7 | 350.6379611 | 0.677258819 |
| 336.7-297.9 | 314.7821036 | 0.775586161 |
| 297.9-293.1 | 295.4222209 | 0.799779319 |
| 293.1-271.2 | 281.2260787 | 0.844974101 |
| 271.2-254.9 | 262.5094171 | 0.885670627 |
| 254.9-241.5 | 247.8251105 | 0.914384164 |
| 241.5-229.9 | 235.3841146 | 0.939107638 |
| 229.9-218.4 | 223.8303393 | 0.963836661 |
| 218.4-143.9 | 165.3652577 | 1.129471233 |
| 143.9-105.5 | 118.3403917 | 1.219663568 |

TABLE XVII-continued

Nitrogen Desorption Data for CY14144

| Pore Diameter Range (Å) | Average Diameter (Å) | Cumulative Pore Volume (cm$^3$/g) |
| --- | --- | --- |
| 105.5-85.5 | 93.18473659 | 1.269908393 |
| 85.5-70.2 | 76.1345754 | 1.313809596 |
| 70.2-59.9 | 64.12468772 | 1.346563035 |
| 59.9-51.8 | 55.16793458 | 1.375536168 |
| 51.8-45.4 | 48.0976978 | 1.401122481 |
| 45.4-40.2 | 42.43389408 | 1.424635177 |
| 40.2-36.1 | 37.88651456 | 1.449718809 |
| 36.1-32.1 | 33.79019728 | 1.477483715 |
| 32.1-28.9 | 30.28159181 | 1.497726602 |
| 28.9-26.3 | 27.45536434 | 1.516706872 |
| 26.3-23.6 | 24.73777781 | 1.540207545 |
| 23.6-21.1 | 22.17739744 | 1.565080566 |
| 21.1-19.0 | 19.93703511 | 1.59109954 |
| 19.0-16.5 | 17.51596978 | 1.630846881 |

TABLE XVIII

Nitrogen Desorption Data for CY15101

| Pore Diameter Range (Å) | Average Diameter (Å) | Cumulative Pore Volume (cm$^3$/g) |
| --- | --- | --- |
| 1633.5-1308.6 | 1434.817706 | 0.015869195 |
| 1308.6-938.9 | 1063.085479 | 0.076011287 |
| 938.9-822.1 | 872.5400938 | 0.113427572 |
| 822.1-664.4 | 726.153686 | 0.190492729 |
| 664.4-541.2 | 589.8410779 | 0.271968628 |
| 541.2-495.4 | 516.2061221 | 0.306797766 |
| 495.4-452.4 | 471.8824199 | 0.342922234 |
| 452.4-411.9 | 430.1606805 | 0.374728484 |
| 411.9-373.7 | 390.8559715 | 0.406903208 |
| 373.7-338.1 | 354.0440222 | 0.436879429 |
| 338.1-306.8 | 320.8627294 | 0.464287882 |
| 306.8-282.0 | 293.2737773 | 0.487609004 |
| 282.0-258.7 | 269.2384186 | 0.507679709 |
| 258.7-244.7 | 251.276503 | 0.519925622 |
| 244.7-229.0 | 236.3042502 | 0.53405423 |
| 229.0-216.9 | 222.6261956 | 0.545016489 |
| 216.9-207.3 | 211.8651212 | 0.55492914 |
| 207.3-144.0 | 163.6239028 | 0.618758477 |
| 144.0-103.4 | 116.4570854 | 0.668697015 |
| 103.4-85.6 | 92.59846579 | 0.694263778 |
| 85.6-72.1 | 77.55016135 | 0.716487235 |
| 72.1-60.7 | 65.25664927 | 0.73733967 |
| 60.7-53.0 | 56.18831893 | 0.752958019 |
| 53.0-46.6 | 49.26725758 | 0.767344784 |
| 46.6-41.5 | 43.64795708 | 0.78015016 |
| 41.5-37.3 | 39.09541737 | 0.794981989 |
| 37.3-33.3 | 35.01993833 | 0.810085989 |
| 33.3-30.2 | 31.57017231 | 0.8201347 |
| 30.2-27.5 | 28.71043051 | 0.829560837 |
| 27.5-24.8 | 25.99331273 | 0.839975544 |
| 24.8-22.6 | 23.59379328 | 0.8493402 |
| 22.6-20.0 | 21.1163566 | 0.861908143 |
| 20.0-17.8 | 18.73336683 | 0.874402144 |

TABLE XIX

Mercury Intrusion Data for CY15101

| Pore size Diameter (A) | Cumulative Intrusion (mL/g) |
| --- | --- |
| 226247.25 | 3.367E−30 |
| 213156.0625 | 0.001661795 |
| 201297.1875 | 0.002658872 |
| 172619.2656 | 0.005317744 |
| 139526.7344 | 0.007976616 |
| 113150.6484 | 0.009638411 |
| 90544.85156 | 0.012297283 |
| 78737.24219 | 0.014125257 |

TABLE XIX-continued

Mercury Intrusion Data for CY15101

| Pore size Diameter (A) | Cumulative Intrusion (mL/g) |
| --- | --- |
| 72447.07031 | 0.015620873 |
| 60339.52344 | 0.017947385 |
| 49556.56641 | 0.01949878 |
| 38738.37109 | 0.021929506 |
| 31002.00586 | 0.023903539 |
| 25333.7832 | 0.02616792 |
| 20724.62109 | 0.029177248 |
| 16168.99121 | 0.033409968 |
| 13230.375 | 0.037765641 |
| 10563.43555 | 0.044586275 |
| 8346.731445 | 0.054462213 |
| 6776.340332 | 0.0666546 |
| 5536.147949 | 0.083998173 |
| 4342.036621 | 0.107802272 |
| 3501.501953 | 0.137485042 |
| 2837.420654 | 0.177576199 |
| 2594.672363 | 0.200087309 |
| 2269.617432 | 0.233489379 |
| 1831.204224 | 0.295208424 |
| 1510.503906 | 0.360582143 |
| 1395.643555 | 0.392902017 |
| 1293.973755 | 0.421268374 |
| 1207.494141 | 0.447410613 |
| 1131.894531 | 0.47241658 |
| 1065.193237 | 0.49649471 |
| 953.9039307 | 0.535679519 |
| 884.3017578 | 0.568524599 |
| 823.786377 | 0.597846568 |
| 771.5706177 | 0.616960466 |
| 722.1925049 | 0.691450536 |
| 684.2458496 | 0.697761118 |
| 672.2320557 | 0.703246117 |
| 636.7992554 | 0.713504672 |
| 604.4926758 | 0.726847529 |
| 558.8725586 | 0.746505737 |
| 517.9966431 | 0.774387836 |
| 483.9524536 | 0.799027622 |
| 453.7037354 | 0.824069798 |
| 426.9303894 | 0.846621335 |
| 403.1401672 | 0.898474514 |
| 382.6773987 | 0.91877532 |
| 362.9386292 | 0.946397841 |
| 342.2199707 | 0.946397841 |
| 330.153656 | 0.953894079 |
| 315.6123962 | 0.954481184 |
| 302.6812439 | 0.954481184 |
| 290.4436646 | 0.967425823 |
| 279.009491 | 0.974567354 |
| 268.8323975 | 0.974567354 |
| 259.2565308 | 0.974567354 |
| 241.9353333 | 1.028741002 |
| 226.8330078 | 1.048289418 |
| 213.444046 | 1.065926313 |
| 201.5080414 | 1.074228048 |
| 195.0001221 | 1.095143437 |
| 188.9437103 | 1.106776357 |
| 180.6530914 | 1.11556828 |
| 172.9412994 | 1.127364159 |
| 164.9789429 | 1.139592171 |
| 157.7405396 | 1.150992036 |
| 151.1612091 | 1.161784291 |
| 143.9489746 | 1.172875285 |
| 138.4779053 | 1.185242534 |
| 132.8603821 | 1.194525123 |
| 129.5736542 | 1.200321555 |
| 126.4793472 | 1.207967401 |
| 124.2483292 | 1.213427901 |
| 120.9080048 | 1.221876502 |
| 117.3827286 | 1.223723292 |
| 114.771225 | 1.23161757 |
| 111.937149 | 1.237899184 |
| 108.9081039 | 1.239180923 |
| 106.6535568 | 1.245096564 |
| 104.5474396 | 1.24916625 |
| 102.455368 | 1.25267899 |
| 100.1680145 | 1.261325955 |

TABLE XIX-continued

Mercury Intrusion Data for CY15101

| Pore size Diameter (A) | Cumulative Intrusion (mL/g) |
|---|---|
| 98.2784729 | 1.261325955 |
| 96.45231628 | 1.267885208 |
| 94.40316772 | 1.274962544 |
| 91.53180695 | 1.279593945 |
| 89.26702118 | 1.285915971 |
| 87.08314514 | 1.285915971 |
| 85.42582703 | 1.287682652 |
| 83.6335144 | 1.29400897 |
| 82.10058594 | 1.300267935 |
| 79.91345978 | 1.30387032 |
| 78.01080322 | 1.308264375 |
| 76.19985962 | 1.313777924 |
| 75.09228516 | 1.318249345 |
| 73.41210175 | 1.321508646 |
| 72.23653412 | 1.323805094 |
| 71.09803772 | 1.32500124 |
| 69.86273193 | 1.334167719 |
| 68.40810394 | 1.336985707 |
| 67.13769531 | 1.340026617 |
| 66.03487396 | 1.340026617 |
| 65.0819931 | 1.340224981 |
| 64.04338074 | 1.340224981 |
| 62.38589478 | 1.346690297 |
| 61.32817841 | 1.358168244 |
| 60.30670166 | 1.358168244 |
| 59.41316605 | 1.358532906 |
| 58.54763031 | 1.358532906 |
| 57.79816818 | 1.358532906 |
| 56.88824844 | 1.358532906 |
| 55.92269516 | 1.366921306 |
| 54.98662186 | 1.373521209 |

EXAMPLE 5

Mild Sulfonation of Poly(Divinylbenzene) Based Uncoated Porous Polymeric Beads With Acetyl Sulfate, Followed by Functionalization With Poly(N-Vinylpyrrolidone) as a Hemocompatible Coating, Used to Prepare Modified Polymer CY15048

The general description and the following detailed description are exemplary and explanatory only and are not restrictive of the invention, as defined in the appended claims. Other aspects of the present invention will be apparent to those skilled in the art in view of the detailed description of the invention as provided herein.

Among various "mild" sulfonating agents acetyl sulfate (prepared from 98% conc. Sulfuric acid and acetic anhydride at low temperatures) is known to be very efficient for DVB or styrene based polymeric materials. Sulfonation is usually done at 50° C. for several hours using equimolar amounts of acetyl sulfate and DVB or styrene based polymers. Sulfonation occurs mainly at benzene ring and unreacted double bonds (in DVB based cross-linked polymeric porous beads) could be preserved for further functionalization. Usually after sulfonation with acetyl sulfate, the polymer is converted into $\sim SO_3Na$ form and can be graft copolymerized with N-vinyl pyrrolidone (in bulk with benzoyl peroxide as initiator) or in water solutions (using sodium persulfate initiator). Resulting sulfonated polymer is "coated" with poly(N-vinylpyrrolidone) to make hemocompatible material capable of removing $K^+$ cations from physiological fluids.

The base polymer selected for this modification was polymer CY15044. The sulfonation and workup were carried out as described in Example 4, using 45.0 g dry CY15044 polymer, 150 mL glacial acetic acid, 62.0 g acetic anhydride, and 40.0 g concentrated sulfuric acid. The resulting sulfonated polymer, in $\sim SO_3Na$ form, was rewet in DI water in a 1 L jacketed reaction vessel fitted with a Teflon coated agitator. DI water was removed from the vessel, and a solution composed of 75 mL NVP monomer, 1.7 g sodium persulfate, and 25 mL DI water was added. The reaction was allowed to proceed for 72 hours at 70° C. with agitation speed set to 100 RPM. Resulting poly(NVP) coated polymer was washed five times using 200 mL DI water, and dried in a vacuum oven until no further loss on drying was observed. Cumulative pore volume data for polymer CY15048 is shown below, in Table XX. A log differential pore volume plot is shown in FIG. 7.

Thrombogenicity was measured by the uPTT assay in which materials were compared to the negative control (plasma alone), positive control (glass beads) and reference beads to determine the degree of contact activation activity. In the uPTT assay, the % change in clot formation over time as compared to the reference materials was determined, then grouped according to: <25% activators, 25-49% moderate activators, 50-74% mild activators, 75-100% minimal and >100% non-activators of the intrinsic coagulation pathway. Polymer CY15048, 94%, was a minimal activator.

TABLE XX

Nitrogen Desorption Data for CY15048

| Pore Diameter Range (Å) | Average Diameter (Å) | Cumulative Pore Volume (cm³/g) |
|---|---|---|
| 4355.2-828.4 | 944.3942734 | 0.0001057 |
| 828.4-474.0 | 558.6159743 | 0.000283797 |
| 474.0-303.3 | 351.2170892 | 0.000357942 |
| 303.3-224.3 | 251.4508466 | 0.000719278 |
| 224.3-216.6 | 220.2880162 | 0.001144201 |
| 216.6-208.1 | 212.161881 | 0.001932015 |
| 208.1-143.6 | 163.4823625 | 0.075370749 |
| 143.6-108.1 | 120.3913517 | 0.239861146 |
| 108.1-81.7 | 90.85045572 | 0.292261423 |
| 81.7-71.8 | 76.00202402 | 0.305608258 |
| 71.8-60.2 | 64.83123041 | 0.320783836 |
| 60.2-52.6 | 55.8248996 | 0.329250736 |
| 52.6-46.6 | 49.1740518 | 0.335209946 |
| 46.6-41.3 | 43.5462226 | 0.339923553 |
| 41.3-37.4 | 39.07691383 | 0.349323983 |
| 37.4-32.5 | 34.52204235 | 0.351977397 |
| 32.5-29.4 | 30.76412188 | 0.352966945 |
| 29.4-27.3 | 28.24001433 | 0.353787455 |
| 27.3-24.6 | 25.76447932 | 0.355166927 |
| 24.6-22.3 | 23.26898468 | 0.357207636 |
| 22.3-19.9 | 20.87422635 | 0.360962494 |
| 19.9-17.5 | 18.46778237 | 0.367188172 |

EXAMPLE 6

Mild Sulfonation of Poly(Styrene-co-Divinylbenzene) Uncoated Porous Polymeric Beads, Followed by Functionalization With Poly(N-Vinylpyrrolidone) as a Hemocompatible Coating, Used to Prepare Modified Polymer CY15049

The general description and the following detailed description are exemplary and explanatory only and are not restrictive of the invention, as defined in the appended claims. Other aspects of the present invention will be apparent to those skilled in the art in view of the detailed description of the invention as provided herein.

The base polymer selected for this modification was polymer CY15042. The sulfonation and workup were carried out as described in Example 4, using 45.0 g dry CY15042 polymer, 200 mL glacial acetic acid, 62.0 g acetic anhydride, and 40.0 g concentrated sulfuric acid. The reaction was allowed to proceed for 2 hours. The resulting dried sulfonated polymer, in ~$SO_3Na$ form, was added to a 1 L jacketed reaction vessel fitted with a Teflon coated agitator. 140.0 g N-vinylpyrrolidone monomer and 2.0 g benzoyl peroxide were added to the reactor. The reaction was allowed to proceed for 24 hours at 70° C. with agitation speed set to 100 RPM. Resulting poly(N-vinylpyrrolidone) coated polymer was washed five times using 200 mL DI water, and dried in a vacuum oven until no further loss on drying was observed. Table XXI, below, displays cumulative pore volume data for polymer CY15049. FIG. 8 presents a log differential pore volume plot.

TABLE XXI

Nitrogen Desorption Data for CY15049

| Pore Diameter Range (Å) | Average Diameter (Å) | Cumulative Pore Volume ($cm^3/g$) |
|---|---|---|
| 6798.1-997.4 | 1113.294549 | 0.002499046 |
| 997.4-529.0 | 628.6356118 | 0.005782394 |
| 529.0-503.0 | 515.3445059 | 0.00652485 |
| 503.0-431.3 | 461.4274588 | 0.007796961 |
| 431.3-320.8 | 359.3702778 | 0.010896953 |
| 320.8-317.4 | 319.0643487 | 0.011833304 |
| 317.4-274.0 | 292.3669097 | 0.013396248 |
| 274.0-230.2 | 248.1049882 | 0.016483381 |
| 230.2-225.4 | 227.7447013 | 0.017366617 |
| 225.4-211.6 | 218.0383103 | 0.018833905 |
| 211.6-195.5 | 202.8978228 | 0.029306436 |
| 195.5-143.0 | 160.6741284 | 0.494786051 |
| 143.0-99.0 | 112.5005572 | 0.779812896 |
| 99.0-82.5 | 89.05063735 | 0.848450234 |
| 82.5-69.8 | 74.92200629 | 0.902458565 |
| 69.8-59.0 | 63.37885992 | 0.947842682 |
| 59.0-51.2 | 54.4553105 | 0.981969695 |
| 51.2-44.8 | 47.47101253 | 1.011973922 |
| 44.8-39.4 | 41.69146063 | 1.039279282 |
| 39.4-35.3 | 37.10279099 | 1.066468142 |
| 35.3-31.3 | 33.03019211 | 1.096075821 |
| 31.3-28.2 | 29.57468036 | 1.118921801 |
| 28.2-25.5 | 26.70738162 | 1.143080339 |
| 25.5-22.8 | 23.944141 | 1.17115692 |
| 22.8-20.4 | 21.43590284 | 1.201324419 |
| 20.4-18.2 | 19.13416412 | 1.23163662 |

EXAMPLE 7

Single-Pass Filtration for Hemoglobin and Potassium Removal

The general description and the following detailed description are exemplary and explanatory only and are not restrictive of the invention, as defined in the appended claims. Other aspects of the present invention will be apparent to those skilled in the art in view of the detailed description of the invention as provided herein.

Units of human pRBC were allowed to equilibrate to room temperature for 30 minutes, where the units were gently mixed for 15 minutes. A blood spike was inserted into the unit and samples for the initial hemoglobin (Hb) and potassium concentrations were taken. The blood spike line was attached to the top port of the polymer containing filtration device, and a sample collection line attached to the bottom port. A pinch clamp was fitted on the sample collection line for flow control. Approximately one bed volume, 30 mL, was flushed through the device into a waste container to purge the device of normal saline solution. The sample collection tube was placed over 15 mL conical tubes where 12 mL fractions of pRBCs were collected at a flow rate of about 3-3.5 mL/min until the unit was completely filtered. Sample tubes were centrifuged for 15 minutes at 4600 RPM at 4° C. Plasma supernatant from each sample tube was collected and the plasma free hemoglobin level was determined by an absorbance read at 450 nm and potassium levels were measured with a potassium ion-selective electrode. The percentage of initial free hemoglobin removed during single-pass filtration, averaged from three trials, is presented in FIG. 9. FIG. 10 displays pre- and post-filtration potassium ion concentration in blood, averaged from three trials. Polymers CY15101 and CY15102 are able to remove significant quantities of both potassium and hemoglobin, while polymer CY15100 only removes the potassium and does not remove hemoglobin.

EXAMPLE 8

Dynamic Recirculation Filtration

The general description and the following detailed description are exemplary and explanatory only and are not restrictive of the invention, as defined in the appended claims. Other aspects of the present invention will be apparent to those skilled in the art in view of the detailed description of the invention as provided herein.

Polymer CY14144 has been tested in a dynamic competitive system evaluating albumin (30 mg/mL) and myoglobin (100 mg/L) removal from a PBS solution with 8 mEq/L potassium. This model has been designed to reflect clinical albumin and myoglobin (rhabdomyolysis) values. The dynamic system allows for the continuous measurement of protein adsorption by the polymer beads at two UV wavelengths. As long as the surrogate proteins, such as albumin and myoglobin, have different UV absorption profiles, the two protein surrogates can be measured simultaneously, providing competitive adsorption conditions. This allows a rapid assessment of polymer performance for the simultaneous adsorption of target and non-target factors under flow conditions; a key parameter to assess studies that balance sorption with hemocompatibility. The dynamic system has been fully calibrated (absorbance and flow conditions) and was used to measure binding with a 6 mL polymer filled device at a flow rate of 6 mL/min for five hours at room temperature. CY14144 has a robust myoglobin adsorption, potassium removal and demonstrated good selectivity with minimal albumin removal. Dynamic recirculation data for CY14144, averaged from 7 trials, is shown below in FIG. 11. The average potassium removal, measured as the percent reduction from initial quantity, was found to be 25.3% with a standard deviation of 1.42.

Thrombogenicity was measured by the uPTT assay in which materials were compared to the negative control (plasma alone), positive control (glass beads) and reference beads to determine the degree of contact activation activity. In the uPTT assay, the % change in clot formation over time as compared to the reference materials was determined, then grouped according to: <25% activators, 25-49% moderate activators, 50-74% mild activators, 75-100% minimal and >100% non-activators of the intrinsic coagulation pathway. Shown below, in Table XXII, is a comparison of thrombogenicity for two different potassium removing polymers. Polymer CY14144 exhibits minimal thrombogenic activity while still removing potassium and myoglobin simultaneously in a dynamic recirculation model in phosphate buffered saline (PBS). In comparison, potassium sorbent CY14022 is a moderate activator of the intrinsic coagulation pathway by the uPTT assay and is ineffective in myoglobin removal.

TABLE XXII

Myoglobin and Potassium Removal from PBS in a Dynamic Recirculation Model

| Polymer | uPTT | Myoglobin Removal | Potassium Removal |
|---|---|---|---|
| CY14144 | 87% | 71.63% | 25.3% |
| CY14022 | 59% | 5.94% | 66.07% |

The general description and the following detailed description are exemplary and explanatory only and are not restrictive of the invention, as defined in the appended claims. Other aspects of the present invention will be apparent to those skilled in the art in view of the detailed description of the invention as provided herein.

Additionally, polymer CY14144 is able to remove significant levels of potassium from blood plasma in a dynamic recirculation model. The normal range for blood potassium is 3.5-5 mEq/L while a patient suffering from hyperkalemia might have blood potassium levels up to 7-7.5 mEq/L. Reperfusion of plasma with a starting concentration of potassium 7.45 mEq/L through a device filled with polymer CY14144 under recirculation conditions that mimic the clinical application reduced the potassium concentration to 4.52 mEq/L (a 2.93 mEq/L reduction) in 5 hours.

The general description and the following detailed description are exemplary and explanatory only and are not restrictive of the invention, as defined in the appended claims. Other aspects of the present invention will be apparent to those skilled in the art in view of the detailed description of the invention as provided herein.

What is claimed is:

1. A method of removing 1) at least one of protein based toxins and inflammatory mediators; and 2) positively charged ions, the method comprising
   contacting a physiological fluid with a biocompatible polymer system comprising at least one polymer, the at least one polymer comprising (i) a plurality of pores and (ii) a sulfonic acid salt functionality;
   wherein the at least one polymer is in the form of hypercrosslinked or a macroreticular porous polymer that has been sulfonated under mild conditions that retain residual functionality of any unreacted double bonds and chloromethyl groups.

2. The method of claim 1, wherein the said toxins and inflammatory mediators have a molecular weight of from about 0.5 kDa to about 1,000 kDa.

3. The method of claim 1, wherein the said toxins and inflammatory mediators have a molecular weight of from about 1 kDa to about 1,000 kDa.

4. The method of claim 1, wherein the at least one polymer's pore structure has a total volume of pore sizes in the range of from 10 A to 40,000 A greater than 0.1 cc/g and less than 5.0 cc/g dry polymer.

5. The method of claim 1, wherein the at least one polymer is hemocompatible.

6. The method of claim 1, wherein an agent is used to imbue biocompatibility that is either (i) heparin or (ii) a heparin mimicking polymer.

7. The method of claim 1, wherein the at least one polymer is formed and subsequently made to be biocompatible.

8. The method of claim 7, wherein an agent used to imbue biocompatibility is either (i) heparin or (ii) a heparin mimicking polymer.

9. The method of claim 1, wherein the polymer system has the form of a solid support.

10. The method of claim 9, wherein the solid support is a bead, fiber, monolithic column, film, membrane, or semipermeable membrane.

11. The method of claim 1, wherein the toxins and inflammatory mediators comprise of one or more of cytokines, superantigens, monokines, chemokines, interferons, proteases, enzymes, peptides including bradykinin, soluble CD40 ligand, bioactive lipids, oxidized lipids, cell-free hemoglobin, cell-free myoglobin, DAMPS, growth factors, glycoproteins, prions, toxins, bacterial and viral toxins, PAMPS, endotoxins, drugs, vasoactive substances, foreign antigens, antibodies, and positively charged ions.

12. The method of claim 9, wherein the solid support has a biocompatible hydrogel coating.

13. The method of claim 1, wherein the positively charged ion is potassium.

14. The method of claim 1, wherein the at least one polymer is made using suspension polymerization, emulsion polymerization, bulk polymerization, or precipitation polymerization.

15. The method of claim 1, wherein the at least one polymer is a hypercrosslinked polymer.

16. The method of claim 1, wherein the unreacted double bonds or chloromethyl groups can be modified via free radical or SN type chemistry to attach one or more of biocompatible and hemocompatible monomers, cross-linkers or low molecular weight oligomers.

17. The method of claim 1, wherein the at least one polymer comprises sulfonic acid groups or a salt thereof, sulfonyl chloride, or sulfonate ester groups.

18. The method of claim 17, wherein the at least one polymer comprising sulfonic acid groups or a salt thereof, sulfonyl chloride, or sulfonate ester groups is produced by graft copolymerization of (i) premade porous polymer that contains unreacted double bonds with (ii) polymerizable vinyl monomers containing sulfonic acid groups or a salt thereof to form a mixture comprising hemocompatible vinyl monomers.

19. The method of claim 1, wherein the biocompatible polymer system is constructed from polymerizable vinyl monomers containing sulfonic acid groups or a salt thereof which are copolymerized in the presence of cross-linker, hemocompatible monomer, monomer and suitable porogen to yield porous polymeric polymer containing a sulfonic acid salt functionality.

20. The method of claim 1, wherein the at least one polymer is housed in a container suitable to retain the polymer and for transfusion of whole blood, packed red blood cells, platelets, albumin, plasma or any combination thereof.

21. The method of claim 1, wherein the at least one polymer is in a device suitable to retain the polymer and be incorporated into an extracorporeal circuit.

* * * * *